US008173606B2

(12) United States Patent
Ferro et al.

(10) Patent No.: US 8,173,606 B2
(45) Date of Patent: *May 8, 2012

(54) SULFATED OLIGOSACCHARIDE DERIVATIVES

(75) Inventors: Vito Ferro, Mt. Ommaney (AU); Jon Krueger Fairweather, Lara (AU); Tomislav Karoli, Kenmore (AU); Ligong Liu, Eight Mile Plains (AU)

(73) Assignee: Progen Pharmaceuticals Limited, Toowong (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/960,145

(22) Filed: Dec. 3, 2010

(65) Prior Publication Data

US 2011/0130354 A1   Jun. 2, 2011

Related U.S. Application Data

(63) Continuation of application No. 10/591,577, filed as application No. PCT/AU2005/000314 on Mar. 4, 2005, now Pat. No. 7,875,592.

(30) Foreign Application Priority Data

Mar. 4, 2004   (AU) ................................ 2004901103

(51) Int. Cl.
*A61K 31/7034* (2006.01)
*A61K 31/7028* (2006.01)
*A61K 31/7056* (2006.01)
*C07H 11/00* (2006.01)
*C07H 15/08* (2006.01)
*C07H 15/18* (2006.01)

(52) U.S. Cl. ........... 514/25; 514/4.1; 536/4.1; 536/17.4; 536/17.6; 536/18.3

(58) Field of Classification Search .................... 514/25; 536/4.1, 17.4, 17.6, 18.3
See application file for complete search history.

(56) References Cited

U.S. PATENT DOCUMENTS

| 5,739,115 A | 4/1998 | Fugedi et al. |
| 6,143,730 A | 11/2000 | Parish et al. |
| 6,271,215 B1 | 8/2001 | Parish et al. |
| 7,875,592 B2 * | 1/2011 | Ferro et al. ................ 514/25 |

FOREIGN PATENT DOCUMENTS

| EP | 0 338 092 | 9/1991 |
| WO | W096/09828 | 4/1996 |
| WO | WO 96/33726 | 10/1996 |
| WO | WO 98/40081 | 9/1998 |

OTHER PUBLICATIONS

Parish et al, Cardiovascular Drug Reviews, 2004, 22(1), 1-6.*
The Merck Manual, 1992, pp. 1488-1489 and pp. 86-88.*
Wolff, Manfred E. "Burger's Medicinal Chemistry, 5ed, vol. I", John Wiley & Sons, 1995, pp. 975-977.*
Banker, G.S. et al., "Modern Pharmaceutics, 3ed.", Marcel Dekker, New York, 1996, pp. 451 and 596.*
Ferro et al J. Med. Chem. 2003, 46, 4601-08.*
Parish et al Cardiovascular \drug Reviews, 2004, 22(1), 1-6.*
Alban, S. et al. (2001) "Partial synthetic glucan sulfates as potential new antithrombotics: a review." Biomacromolecules 2: 354-361.
Amirkhosravi, A.; et al. (2002) "Tissue factor pathway inhibitor reduces experimental lung metastasis of B16 melanoma." Thromb. Haemost. 87:930-6.
Bytheway et al., (2004).)"Validation of Molecular Docking Calculations Involving FGF-1 and FGF-2," Journal of Medicinal Chemistry 47(7):1683-1693.
Chen, L. And Kong, F. J. (2002) "Efficient and Practical Synthesis of α-(1→3)-Linked Mannohexaose and Mannooctaose" Carbohydr. Chem. 21: 341-353.
Crich et al., (2004) "Direct Chemical Synthesis of beta-D-mannans: the beta-(1-->2) and beta-(1-->4) series.", J. Am. Chem. Soc. 126:14930-14934.
Cochran et al (2003) "Probing the interactions of phosphosulfomannans with angiogenic growth factors by surface plasmon resonance." J. Med. Chem., 46(21): 4601-4608.
Demir, M. et al. (2001) "Anticoagulant and antiprotease profiles of a novel natural heparinomimetic mannopentaose phosphate sulfate (PI-88)." J. Clin. Appl. Thromb. Hemost., 7(2): 131-140.
Fairweather J.K., et al., (2004) "The Synthesis of Phosphorylated Disaccharide Components of the Extracellular Phosphomarran of *Pichia* (Hansenula)*holstii* NRRL Y-2488", Bioorganic & Medicinal Chemistry; 12(23):6063-6075.
Ferro, V. et al. (2001) "Large-scale preparation of the oligosaccharide phosphate fraction of *Pichia holstii* NRRL Y-2448 phosphomannan for use in the manufacture of PI-88." Carbohydr. Res. 332(2): 183-189.
Ferro, V. et al. (2002) "Determination of the composition of the oligosaccharide phosphate fraction of *Pichia* (Hansenula) *holstii* NRRL Y-2448 phosphomannan by capillary electrophoresis and HPLC." Carbohydr. Res. 337 (2):139-146.
Ferro, V. et al. (2003) "The development of the novel angiogenesis inhibitor PI-88 as an anticancer drug" Australas. Biotechnol. 13: 38-39.
Ferro, V. et al. (2004) "The development of inhibitors of heparanase, a key enzyme involved in tumour metastasis, angiogenesis and inflammation" Mini-Rev. Med. Chem. 4: 693-702.
Ferro, V., et al., (2007) "PI-88 and Novel Heparan Sulfate Mimetics Inhibit Angiogenesis", Seminars in Thrombosis and Hemostasis, 33(5): 557-562.
Foxall, C., et al. (1996) "Sulfated malto-oligosaccharides bind to basic FGF, inhibit endothelial cell proliferation, and disrupt endothelial cell tube formation." J. Cell. Physiol., 168(3): 657-667.

(Continued)

*Primary Examiner* — Shaojia Anna Jiang
*Assistant Examiner* — Ganapathy Krishnan
(74) *Attorney, Agent, or Firm* — VLP Law Group LLP; Richard G. A. Bone

(57) ABSTRACT

The invention relates to compounds which are polysulfated oligosaccharide derivatives having activity as inhibitors of heparan sulfate-binding proteins and inhibitors of the enzyme heparanase; methods for the preparation of the compounds; compositions comprising the compounds, and use of the compounds and compositions thereof for the antiangiogenic, anti-metastatic, anti-inflammatory, antimicrobial, anticoagulant and/or antithrombotic treatment, lowering of blood triglyceride levels and inhibition of cardiovascular disease of a mammalian subject.

35 Claims, 1 Drawing Sheet

OTHER PUBLICATIONS

Francis, D. J. et al. (2003). "Blockade of vascular smooth muscle cell proliferation and intimal thickening after balloon injury by the sulfated oligosaccharide PI-88: phosphomannopentaose sulfate directly binds FGF-2, blocks cellular signaling, and inhibits proliferation." Circ. Res. 92(8): e70-e77.

Garegg, et al. (1996) "Synthesis of Oligosaccharides Corresponding to Structures Found in Capsular Polysaccharides of *Cryptococcus neoformans*-II", Bioorganic & Medicinal Chemistry 4(11): 1867-1871.

Gu, et al., (2004) "Synthesis of a 6v-Sulfated Mannopentasaccharide Analogue Related to PI-88", Carbohydrate Research, 339:1155-1162.

Gunalp, A. (1965) "Growth and cytopathic effect of rubella virus in a line of green monkey kidney cells" Proc. Soc. Exp. Biol. Med. 118: 85-90.

Gunay, N. S. et al. (1999) "Heparinoids: structure, biological activities and therapeutic applications." J. Planta Med. 65 (4): 301-306.

Hembrough, T. A. et al. (2001) "Tissue factor pathway inhibitor inhibits endothelial cell proliferation via association with the very low density lipoprotein receptor." J Biol. Chem. 276(15):12241-12248.

Holland, T. C. et al. (1984) "Herpes simplex virus type 1 glycoprotein C-negative mutants exhibit multiple phenotypes, including secretion of truncated glycoproteins." J Virol. 52(2):566-574.

Iversen, P. O. et al. (2002) "Inhibitors of angiogenesis selectively reduce the malignant cell load in rodent models of human myeloid leukemias." Leukemia 16(3):376-381.

Jacobsen, S. (1984) Acta Chem. Scand. Ser. B, Org Chem. Biochem. B38:157-164.

Karlsson, R. et al. (1994) "Kinetic and Concentration Analysis Using BIA Technology" Methods 6(2): 99-110.

Katsuraya, K et al. (1994) "Synthesis of Sulfated Alkyl Malto- and Laminara-Oligosaccharides with Potent Inhibitory Effects on Aids Virus Infection," Carbohydrate Research 260(1):51-61.

Katsuraya, K. et al. (1999) "Synthesis of sulfated oligosaccharide glycosides having high anti-HIV activity and the relationship between activity and chemical structure." Carbohydr. Res. 315(3-4):234-242.

Kerekgyarto, J. et al. (1989) "Synthesis of four structural elements of xylose-containing carbohydrate chains from N-glycoproteins." Carbohydr. Res. 186(1): 51-62.

Khachigian, et al. (2004) "Phosphomannopentaose Sulfate (PI-88): Heparan Sulfate Mimetic with Clinical Potential in Multiple Vascular Pathologies", Cardiovascular Drug Reviews 22(1): 1-6.

Levidiotis, V. et al. (2004) "A synthetic heparanase inhibitor reduces proteinuria in passive Heymann nephritis." J. Am. Soc. Nephrol. 15(11): 2882-2892.

Liu et al. (2002) "Cell Surface Heparan Sulfate and Its Roles in Assisting Viral Infections," Medicinal Research Reviews, 22(1): 1-25.

Mori, M. et al. (1989) "A highly stereoselective and practical synthesis of cyclomannohexaose, Cyclo{→4)-[α-d-Manp-(1→4)-]5-α-d-Manp-(1→}, a manno isomer of cyclomaltohexaose." Carbohydr. Res. 192: 131-146.

Nyberg, K. et al. (2004) "The low molecular weight heparan sulfate-mimetic, PI-88, inhibits cell-to-cell spread of herpes simplex virus." Antiviral Res 63(1): 15-24.

Ogawa, T. et al. (1981) "Inhibition of rabbit renal prostaglandin E2 biosynthesis by chronic potassium deficiency." Carbohydr. Res. 97(2): 205-227.

Ogawa, T. et al. (1981) "Synthesis of a branched d-mannopentaoside and a branched d-mannohexaoside: Models of the outer chain of the glycan of soybean agglutinin." Carbohydr. Res. 93(1): 53-66.

Parish, C. R. et al. (1999) "Identification of sulfated oligosaccharide-based inhibitors of tumor growth and metastasis using novel in vitro assays for angiogenesis and heparanase activity." Cancer Res. 59(14): 3433-3441.

Parish, C. R. et al. (2001) "Heparanase: a key enzyme involved in cell invasion." Biochim. Biophys. Acta, 1471(3):M99-M108.

Parish, C. R. et al. (2004) "Phosphomannopentaose sulfate (PI-88): heparan sulfate mimetic with clinical potential in multiple vascular pathologies." Cardiovascular Drug Reviews, 22(1): 1-6.

Parolis, L. A. et al. (1998) "The extracellular polysaccharide of *Pichia* (Hansenula) *holstii* NRRL Y-2448: the phosphorylated side chains." Carbohydr. Res. 309(1) 77-87.

Pillarisetti S., et al., (1997) "Endothelial Cell Heparanase Modulation of Lipoprotein Lipase Activity", The Journal of Biological Chemistry, 272(25): 15753-15759.

Pillarisetti, S., (2000) "Lipoprotein Modulation of Subendothelial Heparan Sulfate Proteoglycans (Perlecan) and Atherogenicity", Trends in Cardiovascular Medicine, 10(2): 60-65.

Vlodavsky, I. et al. (2001) "Molecular properties and involvement of heparanase in cancer metastasis and angiogenesis." J. Clin. Invest. 108(3): 341-347.

Vreys, V., et al., (2007) "Mammalian heparanase: what is the message?", J. Cell. Mol. Med., 11(3): 452.

Wall, D. et al. (2001) "Characterisation of the anticoagulant properties of a range of structurally diverse sulfated oligosaccharides." Thromb. Res. 103(4): 325-335.

Wessel et al. (1995) "Conformational Flexibility in Highly Sulfated Beta-D-Glucopyranoside Derivatives," Carbohydrate Research 274:1-9.

Wessel, H. P. (1997) "Heparinoid Mimetics" Topics Cuir. Chem. 187: 215-239.

Yu, G. et al. (2002) "Preparation and anticoagulant activity of the phosphosulfomannan PI-88." Eur. J Med. Chem. 37 (10): 783-791.

The Merck Manual of Diagnosis and Therapy 1992, 16th Ed., ISBN-10: 0911910166, Robert Berkow (Editor), Merck Research Laboratories: pp. 86-88, and pp. 1488-1489.

The Merck Manual of Diagnosis and Therapy 1992, 16th Ed., ISBN-10: 0911910166, Robert Berkow (Editor), Merck Research Laboratories: pp. 182-189.

Supplementary European Search Report in EP 05706346, (Feb. 7, 2008).

Article 94(3) Communication (EPO) in EP 05706346.3, dated Jun. 11, 2010.

* cited by examiner

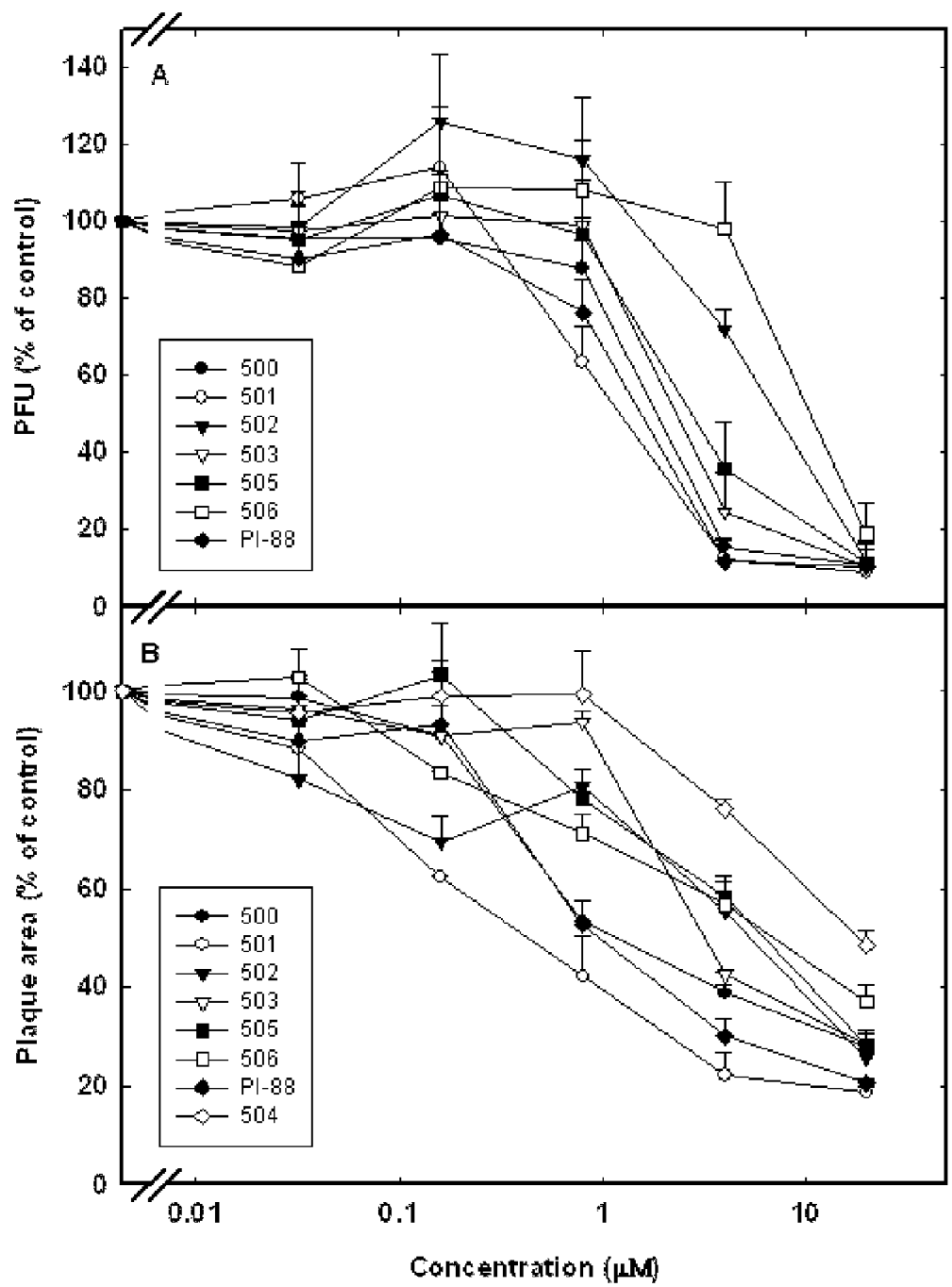

SULFATED OLIGOSACCHARIDE DERIVATIVES

CLAIM OF PRIORITY

This application is a Continuation of U.S. patent application Ser. No. 10/591,577, the entire contents of which are incorporated herein by reference, which application is the U.S. national phase of PCT/AU2005/000314, having an international filing date of Mar. 4, 2005, and claiming benefit of priority to Australian patent application no. 2004901103, filed Mar. 4, 2004.

TECHNICAL FIELD

The invention described herein relates to compounds having activity as inhibitors of heparan sulfate-binding proteins and as inhibitors of the enzyme heparanase. In particular, the invention is directed to sulfated oligosaccharide derivatives, although the scope of the invention is not necessarily limited thereto. Specifically, the invention relates to polysulfated oligosaccharide derivatives, the derivatisation being preferably at C-1 of the reducing end and/or C-6 of the non-reducing end monosaccharide unit. The invention also relates to methods for the preparation of the compounds, compositions comprising the compounds, and use of the compounds and compositions thereof for the antiangiogenic, antimetastatic, anti-inflammatory, antimicrobial, anticoagulant and/or antithrombotic treatment of a mammalian subject. The compounds and compositions thereof also have utility for lowering blood triglyceride levels and inhibiting cardiovascular disease in a mammalian subject. The compounds additionally have utility in the prevention of the foregoing disorders when administered to a mammalian subject.

BACKGROUND ART

The sulfated oligosaccharide agent known as PI-88 [1,2] (see compound 1 below) has been shown to be a promising inhibitor of tumour growth and metastasis [1,3] and is undergoing Phase II clinical trials in cancer patients [4]. PI-88 exerts antiangiogenic effects by inhibiting the interactions of angiogenic growth factors (principally FGF-1, FGF-2 and VEGF) and their receptors with heparan sulfate [1,5]. In addition, PI-88 is a potent inhibitor of the enzyme heparanase, a glycosidase that cleaves the heparan sulfate side chains of proteoglycans that are a major constituent of the extracellular matrix (ECM) and basement membranes surrounding tumour cells [1,2]. Heparanase has been strongly implicated in angiogenesis: it is able to liberate active heparan sulfate-bound angiogenic growth factors from the ECM and is involved in the degradation of the ECM and subsequent tissue remodeling associated with the sprouting of new blood vessels [6]. The degradation of the ECM by heparanase is also crucial in the spread of tumour cells (metastasis) by allowing them to pass into the blood stream and lodge in remote sites where they can form secondary tumours [6,7].

In addition to its antiangiogenic effects, PI-88 inhibits the blood coagulation cascade by (i) inhibiting proteases in the intrinsic pathway, (ii) stimulating the release of tissue factor pathway inhibitor (TFPI), and (iii) activating the heparin cofactor II-mediated inhibition of thrombin. However, PI-88 does not interact with AT III and thus shows no anti-Xa or AT III-mediated anti-IIa activity [8,9]. In vivo studies in monkeys have shown that low doses of PI-88 stimulate release of all heparan sulfate bound TFPI from the vascular cell wall [9]. Apart from its effect on coagulation, TFPI was recently shown to be an antiangiogenic agent [10] and an inhibitor of metastasis [11]. PI-88 has also been shown to block vascular smooth muscle cell proliferation and intimal thickening [12], to inhibit herpes simplex virus (HSV) infection of cells and the cell-to-cell spread of HSV-1 and HSV-2 [13], and to inhibit proteinuria in passive Heymann nephritis [14].

PI-88 is a mixture of highly sulfated, monophosphorylated mannose oligosaccharides ranging in size from di- to hexasaccharide [15,16]. PI-88 is prepared by exhaustive sulfonation [2,16] of the oligosaccharide phosphate fraction (2) (see formula I following this paragraph) obtained by mild, acid-catalyzed hydrolysis of the extracellular phosphomannan of the yeast *Pichia* (Hansenula) *holstii* NRRL Y-2448 [17,18]. The major components are the penta- and tetrasaccharide phosphates 3 (~60%) and 4 (~30%), respectively, whilst the remaining 10% is made up of di-, tri- and hexasaccharide phosphates (5-7) and a tetrasaccharylamine (not shown) [15, 16].

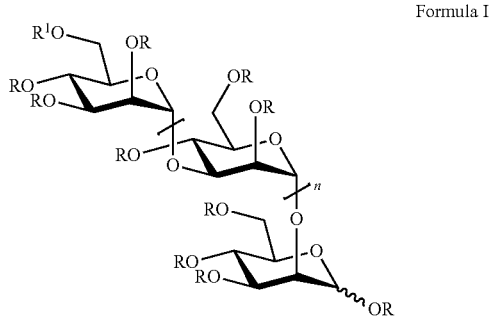

Formula I

| | n | R | R$^1$ |
|---|---|---|---|
| 1 | 0-4 | SO$_3$Na or H | PO$_3$Na$_2$ |
| 2 | 0-4 | H | PO$_3$Na$_2$ |
| 3 | 3 | H | PO$_3$Na$_2$ |
| 4 | 2 | H | PO$_3$Na$_2$ |
| 5 | 0 | H | PO$_3$Na$_2$ |
| 6 | 1 | H | PO$_3$Na$_2$ |
| 7 | 4 | H | PO$_3$Na$_2$ |
| 8 | 0 | H | H |
| 9 | 1 | H | H |
| 10 | 2 | H | H |
| 11 | 3 | H | H |

Various other polysulfated oligo- and polysaccharides and their derivatives are well known to exhibit similar types of biological activities to PI-88 [19-25]. These biological activities are attributed to the inhibition of various heparan sulfate (HS)-binding proteins. The object of the present invention is to create derivatives of PI-88 that have similar biological activities but with improved properties, for example, in their pharmacokinetic and/or ADME (absorption, distribution, metabolism, excretion) profiles. A further object of the invention is to provide compounds comprising a single carbon skeleton to facilitate their synthesis and characterization.

SUMMARY OF THE INVENTION

According to a first embodiment of the invention, there is provided a compound of the general formula:

$$X\text{—}[Y]_n\text{—}Z\text{—}UR^1 \qquad \text{II}$$

wherein;

X, Y and Z are each a monosaccharide unit with a group UR bonded via a single or multiple bond to each non-linking carbon of X, Y and Z, except carbon-1 of monosaccharide Z which bears $UR^1$ bonded via a single or multiple bond;

n is an integer having a value of 0-6;

each U is independently C, N, S or O or their higher oxidation states, including CO, COO, NO, $NO_2$, S(O), S(O)O;

each R is independently $SO_3M$ or H, where M is any pharmaceutically acceptable cation or is any alkyl, aryl, acyl, aroyl, alkyl sulfonyl, aryl sulfonyl, PEG, a PEG derivative, H or the group

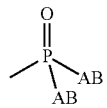

where independently in each AB group, A is O or NH, and B is H, or M where M is as defined above, or an alkyl, aryl or any other suitable group;

$R^1$ is $SO_3M$, H, alkyl, aryl, acyl, aroyl, alkyl sulfonyl, aryl sulfonyl, PEG or a PEG derivative, or $R^1$ together with U is $N_3$ or a substituted triazole or derivative, or a substituted tetrazole or derivative, or a substituted aryl or derivative, or a substituted heteroaryl or derivative;

with the proviso that when all $UR^1$ and UR groups are $OSO_3M$ or OH (excluding the exocyclic methylene group of monosaccharide X), the exocyclic methylene group of monosaccharide X cannot be a $OPO_3M_2$ group.

According to a second embodiment of the invention, there is provided a pharmaceutical or veterinary composition for the prevention or treatment in a mammalian subject of a disorder resulting from angiogenesis, metastasis, inflammation, coagulation/thrombosis, raised blood triglyceride levels, microbial infection and/or cardiovascular disease, which composition comprises at least one compound according to the first embodiment together with a pharmaceutically or veterinarially acceptable carrier or diluent for said at least one compound.

A third embodiment of the invention comprises the use of a compound according to the first embodiment in the manufacture of a medicament for the prevention or treatment in a mammalian subject of a disorder resulting from angiogenesis, metastasis, inflammation, coagulation/thrombosis, raised blood triglyceride levels, microbial infection and/or cardiovascular disease.

According to a fourth embodiment of the invention there is provided a method for the prevention or treatment in a mammalian subject of a disorder resulting from angiogenesis, metastasis, inflammation, coagulation/thrombosis, raised blood triglyceride levels, microbial infection and/or cardiovascular disease, which method comprises administering to the subject an effective amount of at least one compound according to the first embodiment, or a composition comprising said at least one compound.

A further embodiment of the invention comprises novel intermediates and the synthetic pathway resulting in the sulfated oligosaccharides of the first embodiment.

Preferred compounds according to the invention, where the monosaccharide molecules are exclusively D-mannose and the glycosidic linkages are α-(1→2) and α-(1→3), are depicted in the following structure:

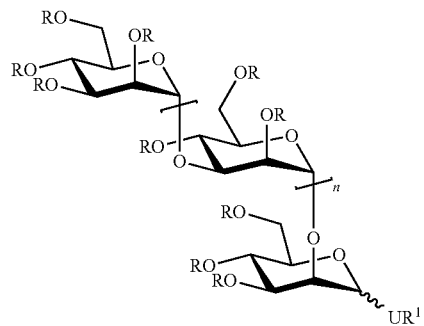

where R, $R^1$, U and n are as defined above.

In order that the invention may be more readily understood and put into practice, one or more preferred embodiments thereof will now be described, by way of example only, with reference to the accompanying FIGURE.

BRIEF DESCRIPTION OF THE DRAWING

FIG. 1 shows the effect of PI-88-like compounds on HSV-1 infectivity (A) and HSV-1 cell-to-cell spread (B). In panel A, the results are expressed as a percentage of the number of viral plaque forming units (PFU) formed in cells infected with the compound-treated virions relative to mock-treated controls. In panel B, the results are expressed as a percentage of the average area of 20 viral plaques formed in the continuous presence of compound relative to mock-treated control cells.

DETAILED DESCRIPTION OF PREFERRED EMBODIMENTS

The present inventors have found that a large number of sulfated oligosaccharide derivatives can be synthesised using a number of different strategies as broadly described below and as illustrated in the examples. These compounds have utility in the prevention or treatment in mammalian subjects of a disorder resulting from angiogenesis, metastasis, inflammation, coagulation, thrombosis, elevated blood triglyceride levels, microbial infection and/or cardiovascular disease. This utility results from the ability of the compounds to block the binding of heparan sulfate-binding proteins to their receptors, or to inhibit the activity of the enzyme heparanase.

With regard to the subject compounds of formula II, the monosaccharide units X, Y and Z can be, for example, any hexose or pentose and can be either a D or L isomer. Such hexoses include glucose, mannose, altrose, allose, talose, galactose, idose and gulose. Such pentoses include ribose, arabinose, xylose and lyxose. The glycosidic linkages of the monosaccharide units can be exclusively of one type or of different types in terms of configuration and linkage.

The pharmaceutically acceptable cation M is preferably sodium.

With regard to integer n, a preferred value is 3 so as to provide a compound which is a pentasaccharide.

A preferred suitable $R^1$ group is n-octyl.

The anomeric configuration, where applicable, at $UR^1$ of compounds of formula II can be either α or β or an anomeric α/β mixture.

With regard to the substituents given above in the definition of compounds of formula II, the term "alkyl", when used alone or in compound words such as "arylalkyl" refers to a straight chain, branched or cyclic hydrocarbon group, preferably $C_{1-20}$, such as $C_{1-10}$. For example, the term "$C_1$-$C_6$alkyl" refers to a straight chain, branched or cyclic alkyl group of 1 to 6 carbon atoms. Examples of "$C_{1-6}$alkyl" include methyl, ethyl, iso-propyl, n-propyl, n-butyl, sec-butyl, t-butyl, n-pentyl, isopentyl, 2,2-dimethylpropyl, n-hexyl, 2-methylpentyl, 2,2-dimethylbutyl, 3-methylpentyl and 2,3-dimethylpropyl, n-hexyl, 2-methylpentyl, 2,2-dimethylbutyl, 3-methylpentyl and 2,3-dimethylbutyl. Examples of cyclic $C_{1-6}$alkyl include cyclopropyl, cyclobutyl, cyclopentyl and cyclohexyl Other examples of alkyl include: heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5- 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8,-9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. An alkyl group may be optionally substituted by one or more optional substituents as herein defined. Optionally, the straight, branched or cyclic hydrocarbon group (having at least 2 carbon atoms) may contain one, two or more degrees of unsaturation so as to form an alkenyl or alkynyl group, preferably a $C_{2-20}$alkenyl, more preferably a $C_{2-6}$alkenyl, or a $C_{2-20}$alkynyl, more preferably a $C_{2-6}$alkynyl. Examples thereof include a hydrocarbon residue containing one or two or more double bonds, or one or two or more triple bonds. Thus, "alkyl" is taken to include alkenyl and alkynyl.

The term "aryl", when used alone or in compound words such as "arylalkyl", denotes single, polynuclear, conjugated or fused residues of aromatic hydrocarbons or aromatic heterocyclic (heteroaryl) ring systems, wherein one or more carbon atoms of a cyclic hydrocarbon residue is substituted with a heteroatom to provide an aromatic residue. Where two or more carbon atoms are replaced, this may be by two or more of the same heteroatom or by different heteroatoms. Suitable heteroatoms include O, N, S and Se.

Examples of "aryl" include phenyl, biphenyl, terphenyl, quaterphenyl, naphtyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl, pyridyl, 4-phenylpyridyl, 3-phenylpyridyl, thienyl, furyl, pyrrolyl, indolyl, pyridazinyl, pyrazolyl, pyrazinyl, thiazolyl, pyrimidinyl, quinolinyl, isoquinolinyl, benzofuranyl, benzothienyl, purinyl, quinazolinyl, phenazinyl, acridinyl, benoxazolyl, benzothiazolyl and the like. Preferred hydrocarbon aryl groups include phenyl and naphthyl. Preferred heterocyclic aryl groups include pyridyl, thienyl, furyl, pyrrolyl. An aryl group may be optionally substituted by one or more optional substituents as herein defined.

The term "acyl" refers to a group —C(O)—R wherein R is an alkyl or aryl group. Examples of acyl include straight chain or branched alkanoyl such as acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanyl; cycloalkylcarbonyl, such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylakanoyl (e.g. phenylaceyl, phenylpropanoyl, phenylbutanoyl, phenylisobutylyl, phenypentanoyl and phenylhexanoyl) and naphthylalkanoyl (e.g. naphthyhlacetyl, naphthylpropanoyl and naphthylbutanoyl). Since the R group may be optionally substituted as described above, "acyl" is taken to refer to optionally substituted acyl.

Optional substituents for alkyl, aryl or acyl include halo (bromo, fluoro, chloro, iodo), hydroxy, $C_{1-6}$alkyl (e.g. methyl, ethyl, propyl (n- and i-isomers)), $C_{1-6}$alkoxy (e.g. methoxy, ethoxy, propoxy (n- and i-isomers), butoxy (n-, sec- and t-isomers), nitro, amino, $C_{1-6}$alkylamino (e.g. methyl amino, ethyl amino, propyl (n- and i-isomers)amino), $C_{1-6}$dialkylamino (e.g. dimethylamino, diethylamino, diisopropylamino), halomethyl (e.g. trifluoromethyl, tribromomethyl, trichloromethyl), halomethoxy (eg trifluoromethoxy, tribromomethoxy, trichloromethoxy) and acetyl.

A 5-6 membered heterocyclyl group includes aromatic 5-6-membered heterocyclic groups (heteroaryl) as described above and non aromatic 5-6-membered heterocyclic groups containing one or more heteroatoms (preferably 1 or 2) independently selected from O, N, S and Se. Examples thereof include dioxanyl, pyranyl, tetrahydrofuranyl, piperidyl, morpholino, piperazinyl, thiomorpholino and saccharides.

The degree of sulfation of compounds according to the invention is typically at least 50%. That is, at least 50% of the R groups of an oligosaccharide derivative comprise $SO_3M$. The degree of sulfation is typically from 70 to 100% and preferably is at least as high as 90%.

The PI-88 derivatives of formula II can be made via a stepwise synthetic route or by starting with the PI-88 backbone already in place (using the readily available compounds 8-11; see formula I above) and making the desired modifications thereto. The inventors determined from a consideration of the structure of PI-88 (1) and its precursor (2), that there are two preferred points of derivatisation: at the reducing end (A) and at the terminal 6-position at the non-reducing end (B) as illustrated in the following structural formula.

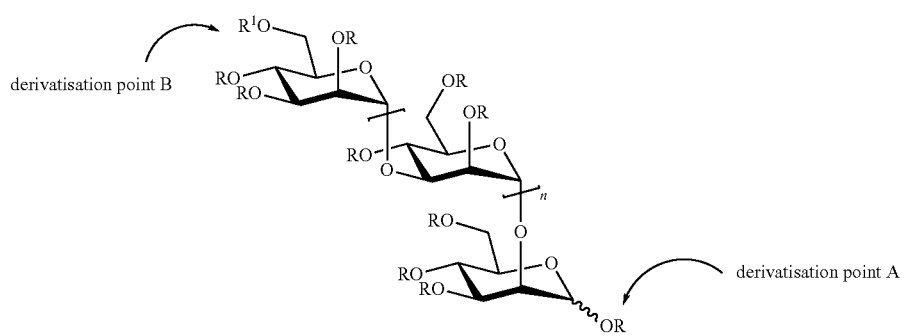

R = SO$_3$Na or H, R$^1$ = PO$_3$Na$_2$, n = 0-4

It should be noted that di-, tri-, tetra- and pentasaccharide (and larger) derivatives all can be made by the same chemistry. However, the pentasaccharide derivatives are preferred since they are the most biologically active [1,2,5,8,13]. All the derivatives made are then subject to deprotection (typically, deacetylation with NaOMe) and the resulting polyol sulfonated with a sulfonating reagent such as sulfur trioxide pyridine complex or sulfur trioxide trimethylamine complex.

As indicated above, the compounds according to the invention have utility in the prevention or treatment in mammalian subjects of a disorder resulting from angiogenesis, metastasis, inflammation, coagulation, thrombosis, elevated blood triglyceride levels, microbial infection or cardiovascular disease. The compounds have particular utility in the treatment of the foregoing disorders in humans. The compounds are typically administered as a component of a pharmaceutical composition as described in the following paragraphs. As will be illustrated below, the compounds show similar or superior activities to PI-88 itself.

Pharmaceutical compositions for oral administration can be in tablet, capsule, powder or liquid form. A tablet can include a solid carrier such as gelatine or an adjuvant or an inert diluent. Liquid pharmaceutical compositions generally include a liquid carrier such as water, petroleum, animal or vegetable oils, a mineral oil or a synthetic oil. Physiological saline solution, or glycols such as ethylene glycol, propylene glycol or polyethylene glycol may be included. Such compositions and preparations will generally contain at least 0.1 wt % of the compound.

Parenteral administration includes administration by the following routes: intravenously, cutaneously or subcutaneously, nasally, intramuscularly, intraocularly, transepithelially, intraperitoneally and topically. Topical administration includes dermal, ocular, rectal, nasal, as well as administration by inhalation or by aerosol means. For intravenous, cutaneous or subcutaneous injection, or injection at a site where treatment is desired, the active ingredient will be in the form of a parenterally acceptable aqueous solution which is pyrogen-free and has suitable pH, isotonicity and stability. Those of skill in the art will be well able to prepare suitable solutions using, for example, solutions of the subject compounds or derivatives thereof.

In addition to the at least one compound and a carrier or diluent, compositions according to the invention can further include a pharmaceutically or veterinarially acceptable excipient, buffer, stabiliser, isotonicising agent, preservative or anti-oxidant or any other material known to those of skill in the art. It will be appreciated by the person of skill that such materials should be non-toxic and should not interfere with the efficacy of the compound(s). The precise nature of any additive may depend on the route of administration of the composition: that is, whether the composition is to be administered orally or parenterally. With regard to buffers, aqueous compositions typically include such substances so as to maintain the composition at a close to physiological pH or at least within a range of about pH 5.0 to 8.0.

Compositions according to the invention can also include active ingredients in addition to the at least one compound. Such ingredients will be principally chosen for their efficacy as anti-angiogenic, anti-metastatic, anti-inflammatory, anti-coagulant, antimicrobial and anti-thrombotic agents, and agents effective against elevated blood triglyceride levels and cardiovascular disease, but can be chosen for their efficacy against any associated condition.

A pharmaceutical or veterinary composition according to the invention will be administered to a subject in either a prophylactically effective or a therapeutically effective amount as necessary for the particular situation under consideration. The actual amount of at least one compound administered by way of a composition, and rate and time-course of administration, will depend on the nature and severity of the condition being treated or the prophylaxis required. Prescription of treatment such as decisions on dosage and the like will be within the skill of the medical practitioner or veterinarian responsible for the care of the subject. Typically however, compositions for administration to a human subject will include between about 0.01 and 100 mg of the compound per kg of body weight and more preferably between about 0.1 and 10 mg/kg of body weight.

The compounds can be included in compositions as pharmaceutically or veterinarially acceptable derivatives thereof. As used herein "derivatives" of the compounds includes salts, coordination complexes with metal ions such as $Mn^{2+}$ and $Zn^{2+}$, esters such as in vivo hydrolysable esters, free acids or bases, hydrates, or prodrugs. Compounds having acidic groups such as phosphates or sulfates can form salts with alkaline or alkaline earth metals such as Na, K, Mg and Ca, and with organic amines such as triethylamine and Tris (2-hydroxyethyl) amine. Salts can also be formed between compounds with basic groups, such as amines, with inorganic acids such as hydrochloric acid, phosphoric acid or sulfuric acid, or organic acids such as acetic acid, citric acid, benzoic acid, fumaric acid, or tartaric acid. Compounds having both acidic and basic groups can form internal salts.

Esters can be formed between hydroxyl or carboxylic acid groups present in the compound and an appropriate carboxylic acid or alcohol reaction partner, using techniques that will be well known to those of skill in the art.

Prodrug derivatives of the compounds of the invention can be transformed in vivo or in vitro into the parent compounds. Typically, at least one of the biological activities of a parent compound may be suppressed in the prodrug form of the compound, and can be activated by conversion of the prodrug to the parent compound or a metabolite thereof. Examples of prodrugs are glycolipid derivatives in which one or more lipid moieties are provided as substituents on the moieties, leading to the release of the free form of the compound by cleavage with an enzyme having phospholipase activity. Prodrugs of compounds of the invention include the use of protecting groups which may be removed in vivo to release the active compound or serve to inhibit clearance of the drug. Suitable protecting groups will be known to those of skill in the art and include an acetate group.

As also indicated above, compounds according to the invention have utility in the manufacture of a medicament for the prevention or treatment in a mammalian subject of a disorder resulting from angiogenesis, metastasis, inflammation, coagulation/thrombosis, microbial infection, elevated blood triglyceride levels and/or cardiovascular disease. Processes for the manufacture of such medicaments will be known to those of skill in the art and include the processes used to manufacture the pharmaceutical compositions described above.

A general description of the synthetic routes to the compounds according to the invention will now be given. For simplicity, in all schemes, figures and tables which follow, $R^1$ will represent an α-(1→3)-linked $Man_4$ tetrasaccharide portion (with or without a terminal 6-O-phospho group), unless otherwise indicated.

General Procedures

Glycoside Derivatives of PI-88 (O-, S- and C-glycosides)

Glycoside derivatives can be readily prepared by activating the oligosaccharide (with or without a terminal 6-O-phospho group) for glycosylation and condensing it with an appropriate alcohol. A suitable method is the Lewis acid-catalysed or promoted reaction of a peracetylated sugar, e.g, 12, with an alcohol acceptor, e.g. to give 13 and 14. Where a more unreactive acceptor is required, a more reactive glycosyl donor needs to be prepared, e.g, the trichloroacetimidate 15 is used to prepare the PEGylated derivatives 16 and 17 (Scheme 1).

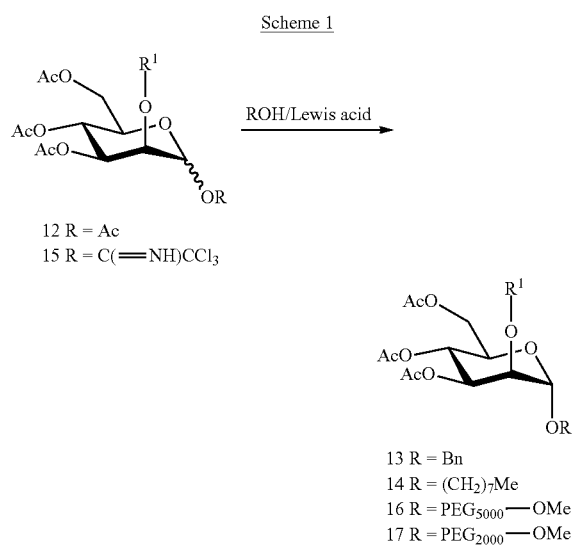

Various other types of donors are known in the art and are suitable as donors, e.g., thioglycosides, halides, n-pentenyl glycosides, selenoglycosides etc. Those skilled in the art will recognize that S- and C-glycosides can be prepared by similar or related methods known in the literature, for example by using an appropriate thiol (or thiol derivative) or a known carbon nucleophile (e.g., allyltrimethylsilane or an appropriate phenol) with a suitably activated donor. The product can then easily be deacetylated and sulfonated. The product of the glycosylation may be a single anomer (α or β) or a mixture of both anomers. Both the pure α and β anomers and the anomeric mixture are suitable for subsequent transformations. This also applies to other derivatives obtained through manipulation of the anomeric centre described in subsequent sections. Therefore, where a single anomer is denoted it is implied that the opposite anomer or a mixture of the two anomers is also claimed. It will also be clear to those skilled in the art that the initially formed glycoside, depending on the nature of the aglycone, can be further derivatized. As an example, if one uses 2-bromohexanol as the alcohol, the product can be converted into an azide (18). This is an extremely versatile compound (Scheme 2) and may further functionalized by, for example, cycloaddition with a compound containing a suitable dipolarophile. Alternatively, the azide can be reduced to an amine and then further functionalized, for example, by alkylation, acylation, a 4-component Ugi condensation etc.

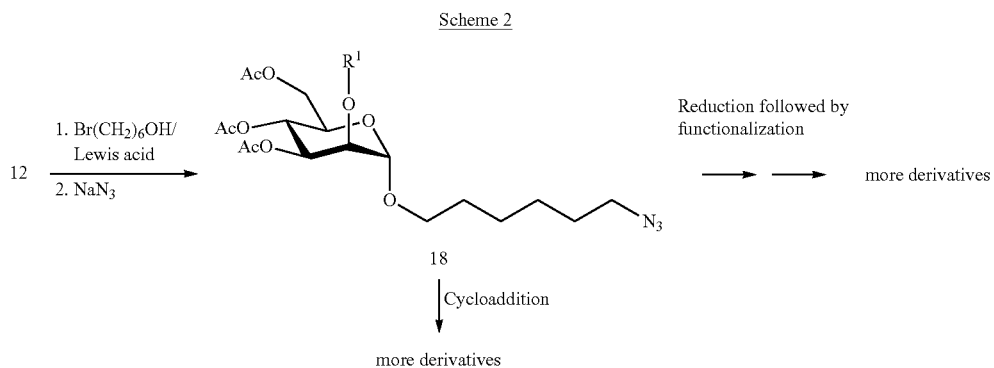

N-Linked Derivatives

From 12, Lewis acid catalysed reaction with TMSN$_3$ leads to the azide 19 (predominantly α). Alternatively, the β-azide 20 can be formed exclusively by initial formation of the α-bromide followed by displacement with NaN$_3$ (Scheme 3). The bromide can also be used as an intermediate for the preparation of thioglycosides or isothiocyanates, for example. The azides can be deprotected and sulfonated as is, or can be reduced and acylated with various acid chlorides to provide a series of glycosyl amides (Scheme 3).

Scheme 3

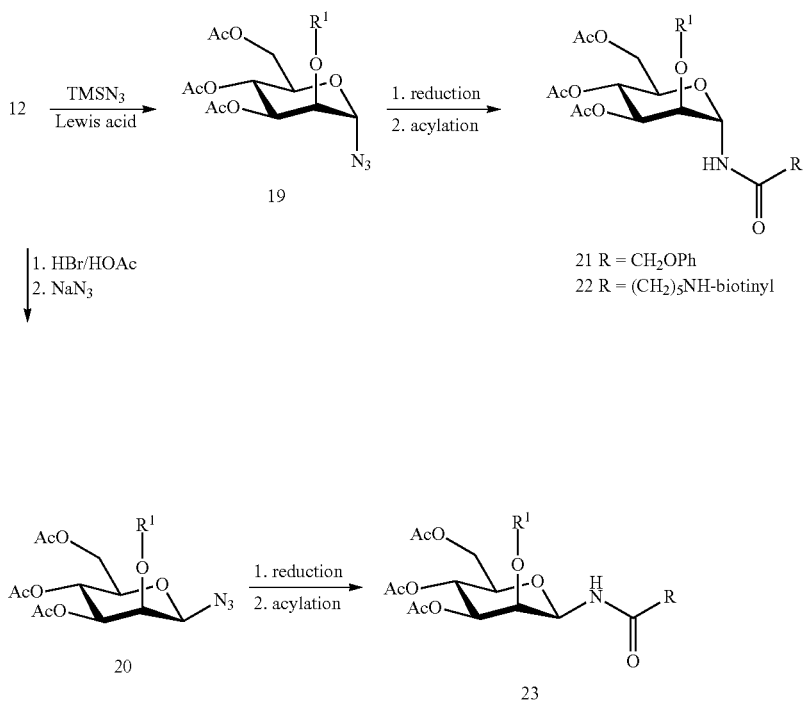

21 R = CH$_2$OPh
22 R = (CH$_2$)$_5$NH-biotinyl

Non-Reducing End Derivatives

Derivatization can also be accomplished at the non-reducing end, for example, by the use of phosphorylated oligosaccharides (either individually or as a mixture) and derivatizing through the phosphate group, e.g., preparation of phosphate esters or phosphoramides. Indeed, suitable compounds can be prepared whereby the reducing end is also derivatized, with either a similar or different functional group.

Having broadly described the invention, non-limiting examples of the compounds, their synthesis, and their biological activities, will now be given.

EXAMPLES

Neutral Manno-Oligosaccharides (a) The manno-oligosaccharides (8) α-D-Man-(1→2)-D-Man, (9) α-D-Man-(1→3)-α-D-Man-(1→2)-D-Man, (10) α-D-Man-(1→3)-α-D-Man-(1→3)-α-D-Man-(1→2)-D-Man, and (11) α-D-Man-(1→3)-α-D-Man-(1→3)-α-D-Man-(1→3)-α-D-Man-(1→2)-D-Man, were isolated from the neutral fraction of the mild acid-catalysed hydrolysis of the extracellular phosphomannan from *P. holstii* NRRL Y-2448 by size exclusion chromatography according to the literature procedure [17]. Alternatively, the oligosaccharides 8-11 were synthesized in a stepwise manner from monosaccharide building blocks as described in example 1 (see below).

(b) Alternatively, the neutral fraction was directly acetylated (excess Ac$_2$O/pyridine) and the individual peracetylated oligosaccharides isolated by flash chromatography (silica gel) and used in this form directly in the next step.

(c) In another approach, the peracetylated mixture from (b) was used directly in the next step and the individual products were then isolated by flash chromatography.

General Procedure for Deacetylation

A solution of the peracetate in anhydrous methanol (0.1 M) was treated with a solution of sodium methoxide in methanol (1.35 M, 0.2-0.6 eq). The mixture was stirred at room temperature for 1-3 h (monitored by TLC). Acidic resin AG®-50W-X8 (H$^+$ form) was added to adjust pH=6-7, the mixture was filtered and the resin was rinsed with methanol. The combined filtrate and washings were concentrated in vacuo and thoroughly dried to give the polyol product.

General Procedure for Sulfonation

A mixture of the polyol and SO$_3$. trimethylamine or SO$_3$.pyridine complex (2 eq. per alcohol) in DMF was heated (60° C., o/n). The cooled (r.t.) reaction mixture was treated with MeOH and then made basic (to pH>10) by the addition of Na$_2$CO$_3$ (10% w/w). The mixture was filtered and the filtrate evaporated and co-evaporated (H$_2$O). The crude polysulfated material was dissolved in H$_2$O and subjected to size exclusion chromatography (see below) to yield the sulfated product. When required, after lyophilisation the product was passed through an ion-exchange resin column (AG®-50W-X8, Na$^+$ form, 1×4 cm, deionized H$_2$O, 15 mL) in order to transfer the product uniformly into the sodium salt form. The solution collected was evaporated and lyophilised to give the final product as a colourless glass or white power.

Size Exclusion Chromatography

Size exclusion chromatography was performed over Bio-Gel P-2 in a 5×100 cm column and a flow rate of 2.8 mL/min of 0.1 M NH$_4^+$.HCO$_3^-$, collecting 2.8 min (7.8 mL) fractions. Fractions were analysed for carbohydrate content by spotting onto silica gel plates and visualisation by charring, and/or analysed for poly-charged species by the dimethyl methylene blue test. Finally, fractions were checked for purity by CE[15] and those deemed to be free of salt were pooled and lyophilised. In the cases of the presence of undersulfated by-products or other organic salt contaminants (normally only small amounts, but quite often detected), an LH20 column chroma-

Example 1

Total Synthesis of Neutral Manno-Oligosaccharides (8-11) from *Pichia*

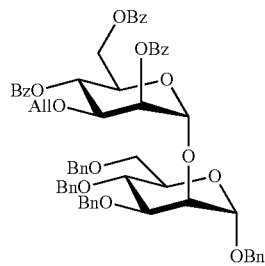

24

Benzyl 2-O-(3-O-Allyl-2,4,6-tri-O-benzoyl-α-D-mannopyranosyl)-3,4,6-tri-O-benzyl-α-D-mannopyranoside (24)

A mixture of 3-O-allyl-2,4,6-tri-O-benzoyl-α-D-mannopyranosyl trichloroacetimidate [26] (902 mg, 1.21 mmol) and benzyl 3,4,6-tri-O-benzyl-α-D-mannopyranoside [27] (723 mg, 1.34 mmol) in 1,2-DCE (10 mL), was stirred in the presence of mol. sieves (1.0 g of 3 Å powder) under an atmosphere of argon (30 min). The mixture was cooled (0° C.) with continued stirring (10 min) prior to the addition of TMSOTf (219 μL, 1.21 mmol). After some time (10 min), Et$_3$N (100 μL) was introduced and the mixture was filtered. The solvent was evaporated and the residue subjected to FC (10-50% EtOAc/hexane) to yield the tribenzoate (24) as, a colourless oil (1.14 g, 84%). $^1$H NMR (CDCl$_3$) δ 3.67-3.81, 3.88-3.95, 4.06-4.15, 4.30-4.35 (4 m, 12 H; H-2$^I$,-3$^I$,-4$^I$,-5$^I$,-6a$^{II}$,-6b$^{II}$,-3$^{II}$,-5$^{II}$,-6a$^{II}$,-6b$^{II}$, OCH$_2$), 4.94-4.70 (m, 7 H; CH$_2$Ph), 4.84 (d, 1 H, J$_{A,B}$ 10.8 Hz; A of AB quartet), 4.93-4.96, 5.04-5.09 (2 m, 2 H; =CH$_2$), 5.02 (d, 1 H, J$_{1,2}$ 1.9 Hz; H-1$^I$), 5.24 (d, 1 H; J$_{1,2}$ 1.9 Ha; H-1$^{II}$), 5.59-5.69 (m, 1 H; =CH), 5.72 (dd, 1 H, J$_{2,3}$ 3.1 Hz; H-2$^{II}$), 5.75 (dd, 1H, J$_{3,4}$ 9.8, J$_{4,5}$ 9.9 Hz; H-4$^{II}$), 7.09-7.58, 7.97-8.06 (2 m, 35 H; Ar). $^{13}$C NMR (CDCl$_3$) δ 61.50, 63.49 (2C; C-6$^I$,-6$^{II}$), 68.63, 69.17, 69.31, 69.46, 69.64, 71.08, 72.04, 72.64, 73.60, 74.73, 75.30, 75.38 (13C; C-3$^I$,-4$^I$,-5$^I$,-2$^{II}$,-3$^{II}$,-4$^{II}$,-5$^{II}$, OCH$_2$, CH$_2$Ph), 79.97 (C-2$^I$), 98.52, 99.60 (C-1$^I$,-1$^{II}$), 117.67 (=CH$_2$), 127.70-138.43 (43C; =CH, Ar), 165.61, 165.69, 166.42 (3C; C=O).

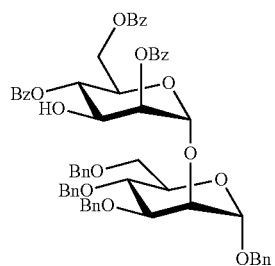

25

Benzyl 2-O-(2,4,6-Tri-O-benzoyl-α-D-mannopyranosyl)-3,4,6-tri-O-benzyl-α-D-mannopyranoside (25)

PdCl$_2$ (40 mg) was added to a solution of the allyl ether (24) (1.09 g, 0.97 mmol) in MeOH (10 mL) and 1,2-DCE (10 mL) and the combined mixture was heated (70°, 40 min). After the time, the solvents were evaporated and the residue subjected to FC (20-30% EtOAc/hexanes) to yield the alcohol (25) as a colourless oil (0.96 g, 91%). $^1$H NMR (CDCl$_3$) δ 3.68-3.81, 3.97-4.06, 4.32-4.71 (3 m, 18 H; H-2$^I$,-3$^I$,-4$^I$,-5$^I$,-6a$^I$,-6b$^I$,-3$^{II}$,-5$^{II}$,-6a$^{II}$,-6b$^{II}$, CH$_2$Ph), 4.84 (d, 1 H, J$_{A,B}$ 12 Hz; A of AB quartet), 5.05 (d, 1 H, J$_{1,2}$ 1.9 Hz; H-1$^I$), 5.26 (d, 1 H; J$_{1,2}$ 1.9 Ha; H-1$^{II}$), 5.61 (dd, 1 H, J$_{2,3}$ 3.3 Hz; H-2$^{II}$), 5.67 (dd, 1 H, J$_{3,4}$ 9.8, J$_{4,5}$ 9.9 Hz; H-4$^{II}$), 7.13-7.40, 7.48-7.59, 7.98-8.06 (3 m, 35 H; Ar). $^{13}$C NMR (CDCl$_3$) δ 60.61, 63.32 (2C; C-6$^I$,-6$^{II}$), 69.06, 69.12, 69.25, 69.44, 70.45, 72.14, 72.65, 72.77, 73.48, 74.79, 75.48, 75.47, 76.23 (13C; C-3$^I$,-4$^I$,-5$^I$,-2$^{II}$,-3$^{II}$,-4$^{II}$,-5$^{II}$, OCH$_2$, CH$_2$Ph), 79.66 (C-2$^I$), 98.34, 99.40 (C-1$^I$,-1$^{II}$), 127.70-138.47 (42C; Ar), 165.97, 166.36, 166.97 (3C; C=O).

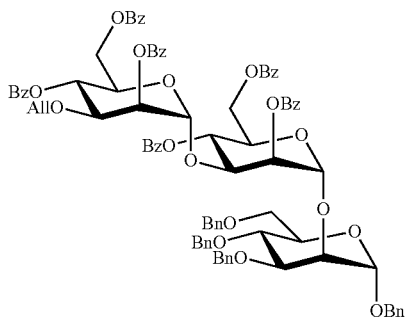

26

Benzyl 2-O-[(3-O-Allyl-2,4,6-tri-O-benzoyl-α-D-mannopyranosyl)-(1→3)-(2,4,6-tri-O-benzoyl-α-D-mannopyranosyl)]-3,4,6-tri-O-benzyl-α-D-mannopyranoside (26)

A mixture of 3-O-allyl-2,4,6-tri-O-benzoyl-α-D-mannopyranosyl trichloroacetimidate (742 mg, 1.01 mmol) and the alcohol (25) (908 mg, 0.84 mmol) in 1,2-DCE (10 mL), was stirred in the presence of mol. sieves (1.0 g of 3 Å powder) under an atmosphere of argon (30 min). The mixture was cooled (0° C.) with continued stirring (10 min) prior to the addition of TMSOTf (181 μL, 1.01 mmol). After some time (10 min), Et$_3$N (100 μL) was introduced and the mixture was filtered. The solvent was evaporated and the residue subjected to FC (10-50% EtOAc/hexane) to yield the hexabenzoate (26) as, a colourless oil (1.26 g, 90%). $^1$H NMR (CDCl$_3$) δ 3.51-3.56, 3.66-4.06, 4.23-4.27, 4.30-42, 4.47-4.72, 4.78-4.86 (6 m, 26 H; H-2$^I$,-3$^I$,-4$^I$,-5$^I$,-6a$^I$,-6b$^I$,-3$^{II}$,-5$^{II}$,-6a$^I$,-6b$^{II}$,-3$^{III}$,-5$^{III}$,-6a$^{III}$,-6b$^{III}$, OCH$_2$, =CH$_2$, CH$_2$Ph), 5.04 (d, 1 H, J$_{1,2}$ 1.7 Hz; H-1$^I$), 5.15 (dd, 1 H, J$_{1,2}$ 1.8, J$_{2,3}$ 2.7 Hz; H-2$^{II}$), 5.26 (d, 1 H; H-1$^{II}$), 5.28 (d, 1 H, J$_{1,2}$ 1.7 Hz; H-1$^{III}$), 5.33-5.43 (m, 1 H; =CH), 5.77-5.82 (m, 2 H; H-4$^{II}$,-2$^{III}$), 5.92 (dd, 1 H, J$_{3,4}$ 9.5, J$_{4,5}$ 9.8 Hz; H-4$^{III}$), 7.00-7.61, 7.80-8.19 (2 m, 50 H; Ar).

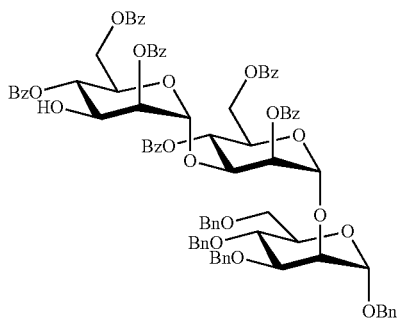

27

Benzyl 2-O-[(2,4,6-Tri-O-benzoyl-α-D-mannopyranosyl)-(1→3)-(2,4,6-tri-O-benzoyl-α-D-mannopyranosyl)]-3,4,6-tri-O-benzyl-α-D-mannopyranoside (27)

PdCl$_2$ (40 mg) was added to a solution of the allyl ether (26) (394 mg, 241 µmol) in MeOH (10 mL) and 1,2-DCE (10 mL) and the combined mixture was heated (70°, 60 min). After the time, the solvents were evaporated and the residue subjected to FC (20-30% EtOAc/hexanes) to yield the alcohol (27) as a colourless oil (317 mg, 84%). $^1$H NMR (CDCl$_3$) δ 3.67-3.82, 3.91-3.99, 4.01-4.21, 4.29-4.71 (4 m, 21 H; H-2$^I$,-3$^I$,-4$^I$,-5$^I$,-6a$^I$,-6b$^I$,-3$^{II}$,-5$^{II}$,-6a$^I$,-6b$^{II}$,-3$^{III}$,-5$^{III}$,-6a$^{III}$,-6b$^{III}$, CH$_2$Ph), 4.83 (d, 1 H, J$_{A,B}$ 10.9 Hz; A of AB quartet), 5.03-5.05 (m, 2 H; H-1$^I$,-2$^{II}$), 5.25-5.28 (m, 2 H; H-1$^{II}$,-1$^{III}$), 5.63 (dd, 1 H, J$_{3,4}$=J$_{4,5}$ 9.9 Hz; H-4$^{II}$), 5.77 (dd, 1 H, J$_{1,2}$ 2.0, J$_{2,3}$ 3.1 Hz; H-2"), 5.92 (dd, 1 H, J$_{3,4}$ 9.7, J$_{4,5}$ 9.9 Hz; H-4$^{III}$), 6.99-7.62, 7.80-8.16 (2 m, 50 H; Ar).

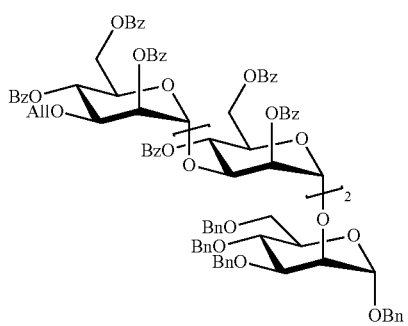

28

Benzyl 2-O-[(3-O-Allyl-2,4,6-Tri-O-benzoyl-α-D-mannopyranosyl)-(1→3)-(2,4,6-tri-O-benzoyl-α-D-mannopyranosyl)]-(1→3)-(2,4,6-tri-O-benzoyl-α-D-mannopyranosyl)]-3,4,6-tri-O-benzyl-α-D-mannopyranoside (28)

A mixture of 3-O-allyl-2,4,6-tri-O-benzoyl-α-D-mannopyranosyl trichloroacetimidate (102 mg, 138 µmol) and the alcohol (27) (135 mg, 86.5 µmol) in 1,2-DCE (6 mL), was stirred in the presence of mol. sieves (100 mg of 3 Å powder) under an atmosphere of argon (30 min). The mixture was cooled (0°) with continued stirring (10 min) prior to the addition of TMSOTf (25 µL, 138 µmol). After some time (10 min), Et$_3$N (100 µL) was introduced and the mixture was filtered. The solvent was evaporated and the residue subjected to FC (10-50% EtOAc/hexane) to yield the nonabenzoate (28) as, a colourless oil (173 mg, 94%). $^1$H NMR (CDCl$_3$) δ 3.44-3.49, 3.60-3.99, 4.05-4.16, 4.42-4.44, 4.48-4.68, 4.73-4.77 (6 m, 30 H; H-2$^I$,-3$^I$,-4$^I$,-5$^I$,-6a$^I$,-6b$^I$,-3$^{II}$,-5$^{II}$,-6a$^{II}$,-6b$^{II}$,-3$^{III}$,-5$^{III}$,-6a$^{III}$,-6b$^{III}$,-3$^{IV}$,-5$^{IV}$,-6a$^{IV}$,-6b$^{IV}$, OCH$_2$, =CH$_2$, CH$_2$Ph), 4.83 (d, 1 H, J$_{A,B}$ 10.9 Hz; A of AB quartet), 5.01-5.04 (m, 2 H; H-1$^I$,-2$^{III}$), 5.19-5.23 (m, 1H; H-2$^{II}$), 5.27-5.40 (m, 4 H; H-1$^I$,-1$^{II}$,-1$^{III}$,=CH$_2$), 5.61 (dd, 1 H, J$_{3,4}$=$_{4,5}$ 9.9 Hz; H-4$^{IV}$), 5.77 (dd, 1 H, J$_{1,2}$ 2.0, J$_{2,3}$ 3.1 Hz; H-2$^{IV}$), 5.90-5.96 (m, 2 H; H-4$^{II}$,-4$^{III}$), 7.01-7.56, 770-8.16 (2 m, 65 H; Ar).

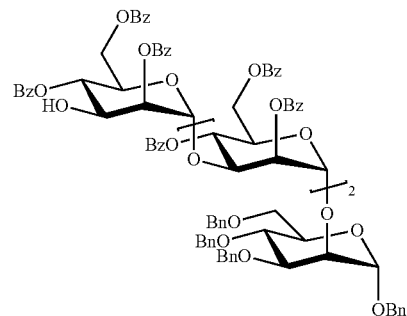

29

Benzyl 2-O-[(2,4,6-Tri-O-benzoyl-α-D-mannopyranosyl)-(1→3)-(2,4,6-tri-O-benzoyl-α-D-mannopyranosyl)]-(1→3)-(2,4,6-tri-O-benzoyl-α-D-mannopyranosyl)]-3,4,6-tri-O-benzyl-α-D-mannopyranoside (29)

PdCl$_2$ (30 mg) was added to a solution of the allyl ether (28) (155 mg, 70.4 µmol) in MeOH (5 mL) and 1,2-DCE (5 mL) and the combined mixture was heated (70°, 40 min). After this time, the solvents were evaporated and the residue subjected to FC (20-40% EtOAc/hexanes) to yield the alcohol (29) as a colourless oil (97 mg, 64%). $^1$H NMR (CDCl$_3$) δ 3.67-3.82, 3.90-4.10, 4.24-4.68 (3 m, 26 H; H-2$^I$,-3$^I$,-4$^I$,-5$^I$,-6a$^I$,-6b$^I$,-3$^{II}$,-5$^{II}$,-6a$^I$,-6b$^{II}$,-3$^{III}$,-5$^{III}$,-6a$^{III}$,-6b$^{III}$,-3$^{IV}$,-5$^{IV}$,-6a$^{IV}$,-6b$^{IV}$, CH$_2$Ph), 4.84 (d, 1 H, J$_{A,B}$ 11.2 Hz; A of AB quartet), 4.86 (d, J$_{1,2}$ 1.8 Hz; H-1$^I$), 4.90 (dd, 1 H; J$_{1,2}$ 1.8, J$_{2,3}$ 3.1 Hz; H-2$^{III}$), 5.03 (d, 1 H, J$_{1,2}$ 1.5 Hz; H-1$^{IV}$), 5.22 (dd, 1 H, J$_{1,2}$ 2.1, J$_{2,3}$ 2.6 Hz; H-2$^{II}$), 5.27-5.29 (m, 2 H; H-1$^{III}$,-1$^{IV}$), 5.46 (dd, 1 H, J$_{3,4}$ 9.7, J$_{4,5}$ 9.9 Hz; H-4"), 5.79 (dd, 1 H, J$_{2,3}$ 2.9 Hz; H-2$^{IV}$), 5.90-5.96 (m, 2 H; H-4$^{II}$,-4$^{III}$), 7.01-7.56, 7.68-8.16 (2 m, 65 H; Ar).

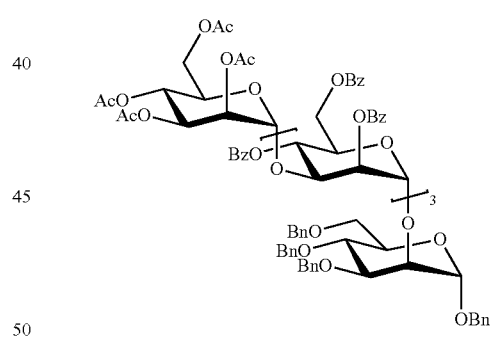

30

Benzyl 2-O-[(2,3,4,6-Tetra-O-Acetyl-α-D-mannopyranosyl)-(1→3)-(2,4,6-tri-O-benzoyl-α-D-mannopyranosyl)]-(1→3)-(2,4,6-tri-O-benzoyl-α-D-mannopyranosyl)-(1→3)-(2,4,6-tri-O-benzoyl-α-D-mannopyranosyl)]-3,4,6-tri-O-benzyl-α-D-mannopyranoside (30)

A mixture of 2,3,4,6-tetra-O-acetyl-α-D-mannopyranosyl trichloroacetimidate [28] (39 mg, 78 µmol) and the alcohol (29) (85 mg, 39 µmol) in 1,2-DCE (3 mL), was stirred in the presence of mol. sieves (100 mg of 3 Å powder) under an atmosphere of argon (30 min). The mixture was cooled (0°) with continued stirring (10 min) prior to the addition of TMSOTf (14.2 µL, 78 µmol). After some time (30 min), Et$_3$N (100 µL) was introduced and the mixture was filtered. The solvent was evaporated and the residue subjected to FC (30-60% EtOAc/hexane) to yield the tetraacetate (30) as, a colourless oil (85 mg, 87%). $^1$H NMR (CDCl$_3$) δ1.82-2.04 (4 s, 3 H each; CH₃CO), 3.67-3.95, 4.05-4.72, 4.82-5.03, 5.21-5.28, 5.69-5.50 (m, 43 H; H-1$^{I-IV}$,-2$^{I-IV}$,-3$^{I-IV}$,4$^{I-IV}$,-5$^{I-IV}$,-6ab$^{I-IV}$, CH₂Ph), 7.01-7.56, 7.68-8.16 (2 m, 65 H; Ar).

General Procedure for Deprotection of the Mannooligosaccharides (25, 27, 29, 30)

(A) A small piece of sodium was added to a solution of the tetrabenzyl ether (25, 27, 29, 30) in MeOH and THF and the combined mixture was stirred (r.t., o/n). After this time, the mixture was neutralised with Dowex 50X8 resin (H⁺) form and filtered. The solvent was evaporated and co-evaporated (MeOH) and used in the following reaction without further purification.

(B) Pd(OH)₂ (10% on C) was added to a solution of the crude product from (A) in THF and H₂O containing a little AcOH (50 L) and the combined mixture was vigorously stirred under hydrogen (100 p.s.i., 3 h). After this time, the mixture was filtered and the solvent evaporated. The residue was subjected to gel filtration chromatography (Biogel P2; H₂O; 60 ml/hr) to yield, after lyophilisation, the mannooligosaccharide (8-11) as a colourless powder. Compounds 8-11 were identical in all respects to those isolated from the *Pichia* hydrolysis as described above.

Example 2

Benzyl Glycoside Polysulfate (PG500)

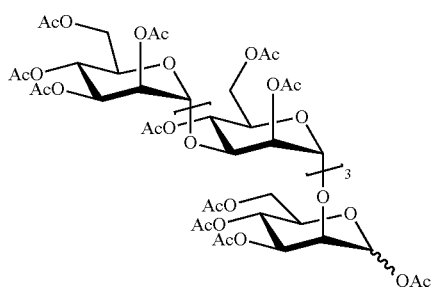

12

Peracetate 12

The pentasaccharide 11 (1.03 g, 95% M5), sodium acetate (1.2 g) and acetic anhydride (50 mL) were heated, with stirring, at 140° C. overnight under a drying tube. The mixture was cooled to room temperature, evaporated to dryness, taken up in EtOAc, washed with brine (×3) and subjected to flash chromatography (40 g silica gel, 80:20 EtOAc:Hx) to yield 810 mg of peracetate 12 as a glass along with less pure material. ¹H NMR (400 MHz, CDCl₃) δ 6.14 (d, 0.84H, J=2.0, αH1$^I$), 5.71 (d, 0.16H, J=0.9, βH1$^I$), 5.30-5.10 (m, 8H), 5.00-4.85 (m, 7H), 4.25-3.70 (m, 19H), 2.20-1.90 (m, 51H). HRMS calcd for C₆₄H₈₇O₄₃ [M+H]⁺ 1543.4623. found 1543.4599.

General Procedure for Direct Glycosylation of Peracetylated Oligosaccharides:

To a solution of the peracetate (eg, 12) (1 eq) in 3 Å MS dried DCM (0.03 M) was added the alcohol (6 eq). In some cases, small amount of powdered 3 Å MS was added. Boron trifluoride etherate (4 eq) was added and the mixture was stirred under an atmosphere of argon at 60° C. or 75° C. for 2 to 26 h. The mixture was cooled and triethylamine was added. The mixture was diluted with dichloromethane, washed with sat. aq. sodium carbonate and dried (anh. MgSO₄). The dried solution was filtered and the cake washed with dichloromethane. The combined filtrate and washings were concentrated, loaded on silica gel and purified by flash chromatography (silica, gradient elution with hexane-EtOAc 6:1 to 1:4) to afford the desired glycoside after evaporation and drying under high vacuum.

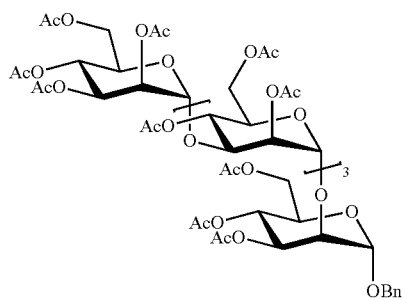

13

Benzyl Glycoside 13

The glycosylation was performed using 12 and benzyl alcohol to give the product (13) as a colourless gum, 108 mg, 46% (Rf=0.32, hexane-EtOAc=1:3). ¹H NMR (CDCl₃, 400 MHz) δ 7.35-7.27 (m, 5H, C₆H₅), 5.30-5.12 (m, 8H), 5.00-4.85 (m, 8H), 4.68 (AB quartet, 1H, J=11.8) and 4.50 (AB quartet, 1H, J=11.8, PhCH₂O), 4.27-3.74 (m, 19H), 2.14 (4), 2.13 (5), 2.13, 2.10, 2.08 (4), 2.07 (9), 2.07 (6), 2.06 (9), 2.06 (6), 2.06 (2×), 2.02, 2.00, 1.99, 1.97, 1.94 (15 s, 48H, 16×Ac); ¹³C NMR (CDCl₃, 100 MHz) δ 171.0, 170.5 (3), 170.5 (1), 170.5 (0), 170.4, 170.3, 170.2, 170.0 (4), 170.0 (2), 169.8 (9), 169.8 (8), 169.7, 169.6, 169.5 (6), 169.4 (6) and 169.3 (total 16×CO), 136.1 (ipso-C₆H₅), 128.5, 128.2 and 127.9 (o, m, p-C₆H₅), 99.2 (2C), 98.9, 98.8, 97.3 (5× sugar-C1), 76.7, 75.1, 74.9 (9), 74.9 (7), 71.1, 70.9, 70.8, 70.2, 69.7, 69.5 (9), 69.5 (6), 69.4 (2), 69.3 (7), 69.2, 68.6, 68.3, 67.1, 66.7 (3), 66.6 (7), 66.1, 65.5, 62.4, 62.1, 61.9, 61.6 and 60.2 (26C, 25× sugar carbons excluding 5× sugar-C1 and benzyl CH₂), 20.9, 20.8 (2), 20.8 (0), 20.7 (8), 20.7, 20.6, 20.5 (4), 20.5 (1), 20.4 (9) and 20.4 (6) (10C, 16×Ac).

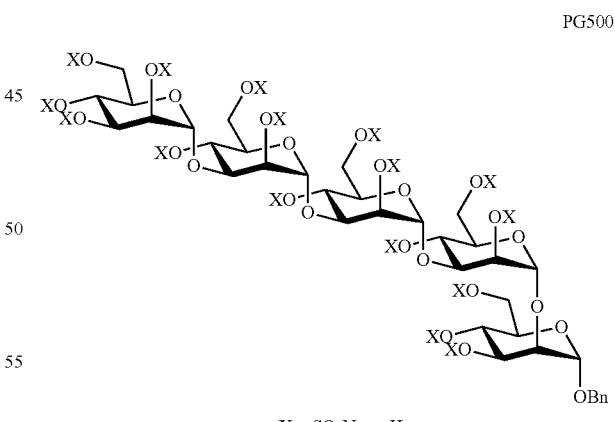

PG500

X = SO₃Na or H

Benzyl Glycoside Polysulfate (PG500)

Compound 13 was deacetylated (HRMS calcd for polyol C₃₇H₅₉O₂₆ [M+H]⁺ 919.3296. found 919.3279) and sulfonated according to the general procedures to give the product (PG500) as a white powder, 76.1 mg, 44%. ¹H NMR (D₂O, 400 MHz) δ 7.35-7.26 (m, 5H, C₆H₅), 5.32 (s, 1H), 5.30 (d, 1H, J=1.2), 5.26 (d, 1H, J=2.0), 5.24 (d, 1H, J=1.6), 5.05 (dd, 1H, J=2.8, 2.0), 5.00 (d, 1H, J=2.0), 4.87-4.85 (m, 2H), 4.68-4.34 (m, 12H), 4.32-3.86 (m, 17H); $^{13}$C NMR (D$_2$O, 100 MHz) δ 137.0, 129.5, 129.4, 129.1, 100.5 (9), 100.5 (6), 100.2, 97.9, 93.8, 76.9, 76.8, 75.6, 75.5 (3), 75.4 (8), 74.4, 73.8, 73.1, 73.0, 72.8, 72.7, 71.8, 71.3, 70.7, 70.6, 70.4, 69.9, 69.8, 69.7, 68.0, 67.8, 67.5, 66.6, 66.3 (7), 66.3 (5).

Example 3

Octyl Glycoside Polysulfate (PG501)

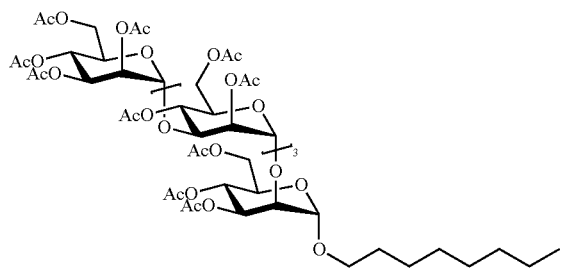

14

Octyl glycoside 14

The glycosylation was performed using 12 and octanol to give the product (14) as a colourless gum, 207 mg, 66% (Rf=0.41, hexane-EtOAc=1:3). $^1$H NMR (CDCl$_3$, 400 MHz) δ 5.23-5.09 (m, 8H), 4.96-4.82 (m, 8H), 4.23-3.71 (m, 19H), 3.59 (dt, 1H, J=9.4, 6.8, OCH$_2$R), 3.35 (dt, 1H, J=9.4, 6.8, OCH$_2$R), 2.11, 2.10 (2), 2.09 (8), 2.06, 2.05, 2.04 (4), 2.04 (1), 2.03 (8), 2.03, 2.02, 2.01, 1.99 (3), 1.98 (8), 1.96, 1.94 and 1.90 (16 s, 48H, 16×Ac), 1.52 (quintet, 2H, J=7.2, CH$_2$), 1.27-1.18 (m, 10H, (CH$_2$)$_5$), 0.80 (t, 3H, J=7.2, CH$_3$); $^{13}$C NMR (CDCl$_3$, 100 MHz) δ 170.4 (0) (2C), 170.3 (8) (2C), 170.3, 170.2, 170.1, 169.9 (2C), 169.8 (2), 169.7 (5), 169.6, 169.5, 169.4 (4), 169.3 (5), 169.3 (16×CO, 3 overlapped), 99.1 (2C), 98.8, 98.7, 98.0 (5× sugar-C1), 77.0, 75.0, 74.8 (3), 74.7 (5), 71.0, 70.8, 70.7, 70.1, 69.4 (9), 69.4 (7), 69.3 (0), 69.2 (7), 69.2, 68.3, 68.2 (0), 68.1 (6), 67.2, 66.6 (4), 66.6 (0), 66.1, 65.4, 62.4, 62.3, 61.8 and 61.5 (25C, sugar carbons excluding sugar-C1 and octyl-CH$_2$O), 31.5, 29.1, 29.0, 28.9, 25.9, 22.4 (6× octyl-CH$_2$), 20.7 (3), 20.7 (0), 20.6 (7), 20.6, 20.5, 20.4 (3), 20.4 (0), 20.3 (9), 20.3 (7) (9C, 16×Ac), 13.85 (octyl-CH$_3$).

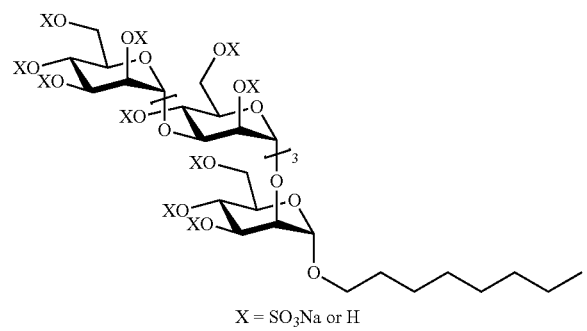

PG501

X = SO$_3$Na or H

Compound 14 was deacetylated (HRMS calcd for polyol C$_{38}$H$_{69}$O$_{26}$ [M+H]$^+$ 941.40784. found 941.4060.) and sulfonated according to the general procedures to give the product (PG501) as a white powder, 195 mg, 72%. $^1$H NMR (D$_2$O, 400 MHz) δ 5.33 (s, 1H), 5.29 (d, 1H, J=1.6), 5.24 (d, 1H, J=1.6), 5.21 (d, 1H, J=1.6), 5.03 (dd, 1H, J=2.8, 2.0), 4.87 (d, 1H, J=1.6), 4.86-4.83 (m, 2H), 4.70-3.92 (m, 27H), 3.59 (dt, 1H, J=9.6, 7.0), 3.44 (dt, 1H, J=9.6, 7.0), 1.48-1.40 (m, 2H), 1.21-1.08 (m, 10H), 0.678 (t, 3H, J=7.2); $^{13}$C NMR (D$_2$O, 100 MHz) δ 100.5, 100.4, 100.1, 100.0, 99.0, 98.4 (1), 98.3 (8), 98.3 (6), 98.3 (5), 76.8 (5), 76.7 (9), 76.7, 76.6, 76.5 (2), 76.4 (7), 76.0, 75.4 (0), 75.3 (5), 75.3, 75.2, 74.3, 73.0 (5), 72.9 (9), 72.7, 72.6, 71.7, 70.4, 70.2, 69.8 (4), 69.7 (5), 69.6, 69.1, 67.8 (5), 67.7 (7), 66.5, 66.2, 31.5, 30.0, 28.8, 25.8, 22.5, 14.0.

Example 4

PEG$_{5000}$ Polysulfate (PG504)

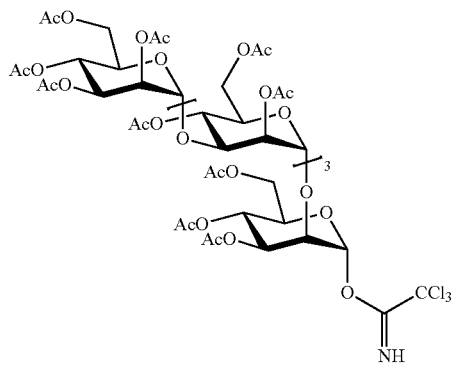

15

Imidate 15

(A) A mixture of the acetate (12) (68 mg, 51 μmol) and BnNH$_2$ (17 μL, 152 μmol) in THF (2 mL), was stirred (r.t.) during some time (2 d). The mixture was diluted with CHCl$_3$ (20 mL) and subjected to work-up. The organic phase was evaporated and co-evaporated (2×10 mL MeCN) and used in the following reaction without further purification.

(B) DBU (10 μL, 6.7 μmol) was added to a solution of the crude product (from A) and trichloroacetonitrile (1.0 mL, 10 mmol) in 1,2-DCE (4 mL) and the combined mixture was stirred (0° C.→12° C., o/n). The mixture was concentrated and the residue subjected to FC (50-90% EtOAc/hexanes) to yield 15 as a pale yellow coloured oil (35 mg, 48%, 2 steps). $^1$H NMR (400 MHz, CDCl$_3$) δ 8.70 (s, 1 H, NH), 6.32 (d, 1H, J=2.0, H1$^I$), 5.36-5.13 (m, 8H), 5.00-4.90 (m, 6H), 4.26-3.75 (m, 20H), 2.15-1.94 (m, 48H).

PG504

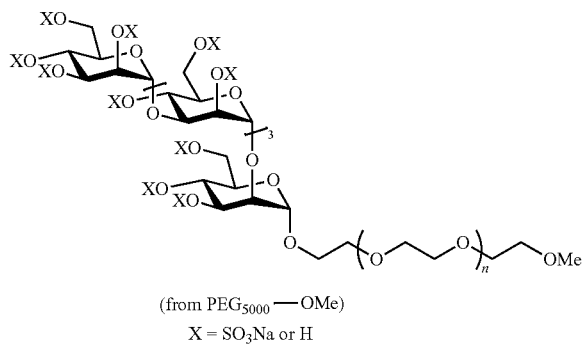

(from PEG$_{5000}$—OMe)

X = SO$_3$Na or H

PEG$_{5000}$ Polysulfate (PG504)

(A) A mixture of the imidate 15 (33 mg, 20.2 μmol) and PEG$_{5000}$-monomethyl ether (151 mg, 30.3 μmol) in 1,2-DCE (3 mL), was stirred in the presence of mol. sieves (50 mg of 3 Å powder) under an atmosphere of argon (10 min). The mixture was cooled (−20° C.) with continued stirring (10 min) prior to the addition of TMSOTf (5 μL, 2.8 μmol). After some time (20 min), Et$_3$N (10 μL) was introduced and the mixture was filtered. The solvent was evaporated and the residue subjected to FC (0-7.5% MeOH/CHCl$_3$) to yield 16 as a colourless glass (104 mg, 80%, based on average M$_r$ 6483). $^1$H NMR (400 MHz, CDCl$_3$) δ 5.28-4.87 (m, 14H), 4.43-3.42 (m, 829 H,), 3.34 (s, 3H, OMe), 2.15-1.94 (m, 48H).

(B) Compound 16 (104 mg, 16 μmol) was deacetylated according to the general procedure to yield Man$_5$-PEG$_{5000}$-OMe as a colourless wax (82 mg, 89%, based on average M$_r$ 5769).

(C) The M$_5$-PEG$_{5000}$-OMe (82 mg, 14 μmol) was sulfonated according to the general procedure to yield PG504 as a colourless foam (45 mg, 42%, based on average M$_r$ 7401). $^1$H NMR (400 MHz, D$_2$O) δ 5.34-4.87 (m, 7H), 4.71-3.97 (m, 20H), 3.76-3.35 (m, 432H), 3.23 (s, 3H, OMe).

Example 5

PEG$_{2000}$ Polysulfate (PG506)

PG506

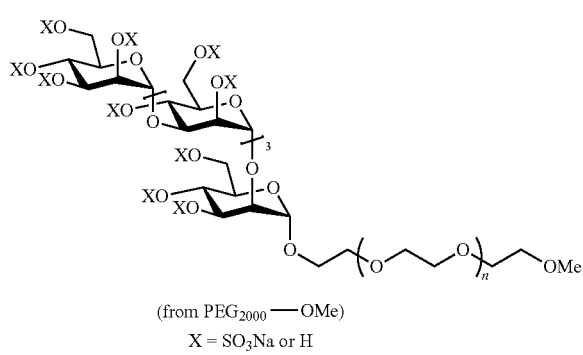

(from PEG$_{2000}$—OMe)

X = SO$_3$Na or H (A) A mixture of the imidate (15) (60 mg, 36.5 μmol) and PEG$_{2000}$-OMe (110 mg, 55.0 μmol) was treated with TMSOTf as described for PEG$_{5000}$-OMe to yield compound 17 as a colourless glass (96 mg, 74%). $^1$H NMR (400 MHz, CDCl$_3$) δ 5.28-5.13, 5.00-4.87, 4.27-3.40 (3 m, many H, H1$^{IV}$,2$^{I-V}$,3$^{I-V}$,4$^{I-V}$,6a$^{I-V}$, OCH$_2$CH$_2$O) 3.34 (s, 3H, OMe), 2.15-1.94 (16 s, 3H each, COMe).

(B) Compound 17 was deacetylated according to the general procedure to yield the PEG$_{2000}$-OMe polyol as a colourless wax (63 mg, 81%). This residue was used in the next reaction without further purification or characterisation.

(C) The product from (B) above was sulfonated according to the general procedure to yield the title compound (PG506) as a colourless powder (47 mg, 68%). $^1$H NMR (400 MHz, D$_2$O) δ 5.34-3.97 (m, 498H), 3.80-3.35 (m, 81H), 3.23 (s, 3H, OMe).

Example 6

PG502

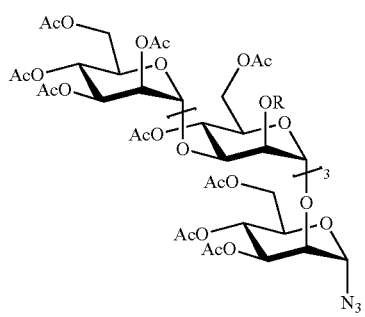

Azide 19

A solution of peracetate 12 (270 mg, 175 μmol), TMSN$_3$ (60 mg, 525 μmol) and SnCl$_4$ (200 μL of 1M in DCM) in anh. DCM (20 mL) was stirred overnight in the dark. Additional quantities (3 eq.) of TMSN$_3$ and SnCl$_4$ were added and stirring was continued in the dark overnight again. Ice and NaHCO$_3$ (sat. aq.) were added and the mixture was extracted with EtOAc, washed with brine, evaporated and subjected to flash chromatography (10 g silica gel, gradient elution, 50:50 to 75:25 EtOAc:Hx) to yield 218 mg (82%) of azide 19. $^1$H NMR (400 MHz, CDCl$_3$) δ 5.52 (d, 1H, J=2.0, H1$^I$), 5.29-5.12 (m, 8H), 5.02-4.87 (m, 7H), 4.29-3.76 (m, 19H), 2.18-1.95 (m, 48H); $^{13}$C NMR (100 MHz, CDCl$_3$) δ 170.5 (9), 170.5 (7), 170.5 (6), 170.4, 170.3, 170.2, 170.1, 169.9 (9), 169.9 (8), 169.9 (5), 169.7 (3), 169.6 (9), 169.6 (6), 169.6, 169.5, 169.3, 99.3 (0), 99.2 (7), 99.1, 99.0, 88.1, 75.2, 75.1, 74.8, 71.1, 70.9, 70.8, 70.6, 69.7, 69.5, 69.4, 69.2, 68.3, 67.3, 66.8, 66.7, 65.5 (9), 65.5 (8), 62.6, 62.2, 62.0, 61.7, 20.8 (8), 20.8 (6), 20.8, 20.7, 20.6 (2), 20.5 (8), 20.5 (7), 20.5. HRMS calcd for C$_{62}$H$_{84}$N$_3$O$_{41}$[M+H]$^+$ 1526.4583. found 1526.4557.

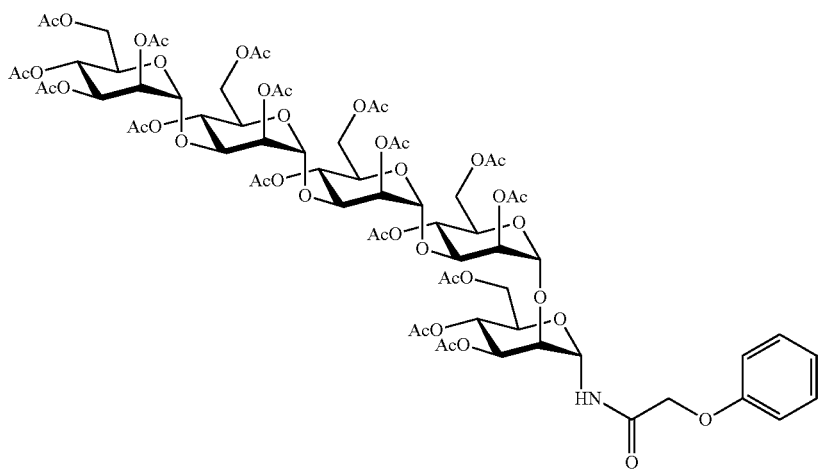

21

1-Deoxy-1-α-phenoxyacetamido peracetate 21

A solution of 19 (32 mg, 21 μmol), PPh$_3$ (11 mg, 42.6 μmol) and phenoxyacetyl chloride (7.3 mg, 43 μmol) in anh. acetonitrile (5 mL) was stirred at 0° C. for 4 h then at r.t. overnight. EtOAc and NaHCO$_3$ (sat. aq.) were added and the organic layer was washed with brine then dried (MgSO$_4$) and subjected to flash chromatography (gradient elution 60:40 to 90:10 EtOAc:Hx) to yield 11.4 mg (33%) of amide 21 with some remaining PPh$_3$/PPh$_3$O. $^1$H NMR (400 MHz, CDCl$_3$) δ 7.36-7.32 (m, 2H), 7.18 (br d, 1H, J=8.1, NH), 7.00-6.90 (m, 3H), 5.79 (dd, 1H, J=3.8, 8.2, H1$^f$), 5.32-4.97 (m, 15H), 4.60-3.76 (m, 21H), 2.20-1.95 (m, 48H, AcO). HRMS calcd for C$_{70}$H$_{92}$NO$_{43}$[M+H]$^+$ 1634.5045. found 1634.5002.

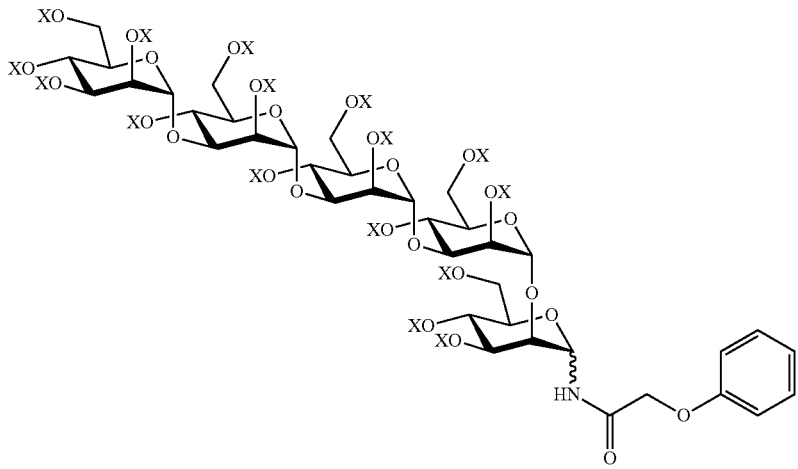

PG502

X = SO$_3$Na or H

PG502

The peracetate 21 (11 mg, 6.7 μmol) was deacetylated and sulfonated according to the general procedures to yield 6 mg (34% for 2 steps) of PG502 after lyophilisation. $^1$H NMR (400 MHz, D$_2$O, solvent suppressed) δ: 7.30-7.21 (m, 2H, ArH'''), 6.96-6.84 (m, 3H, ArH$^{o,p}$), 5.56-3.59 (m, 30H affected by suppression).

Example 7

PG503

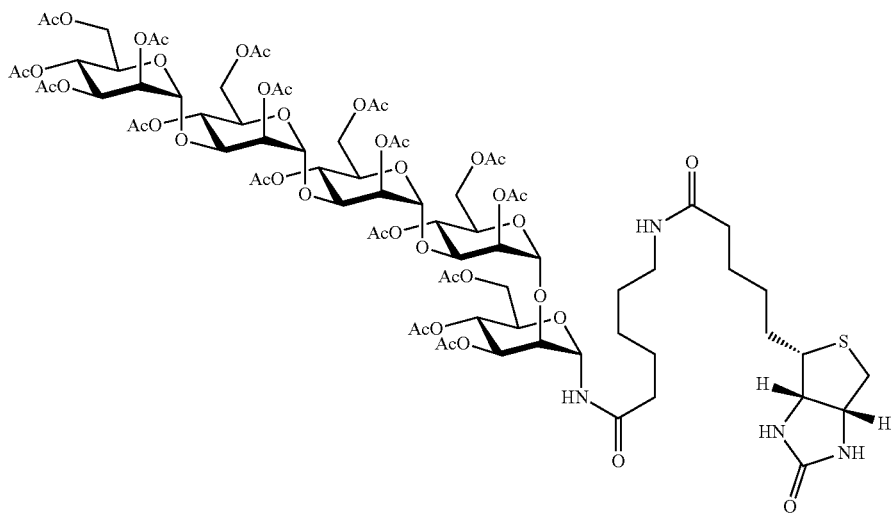

22

1-Deoxy-1-α-Biotinamidocaproamido Peracetate 22

A mixture of 19 (70 mg, 46 μmol) and Adam's catalyst (2 mg) in 2:1 EtOAc:EtOH (3 mL) was stirred under $H_2$ (100 psi) overnight, then filtered, evaporated and co-evaporated with anh. pyridine. Biotinamidocaproate N-hydroxysuccinimide ester (31 mg, 68 μmol) and 1 mL anh. pyridine were added and the mixture was heated to 60° C. for 3 days with stirring. The solution was evaporated and subjected to flash chromatography (9.4 g $Et_3N$ washed silica gel, gradient elution 75:25 EtOAc:Hx to 30:70 MeOH:EtOAc) to give 30.8 mg (36% over two steps) of amide 22. $^1$H NMR (400 MHz, $CDCl_3$) δ 7.41 (br d, 1H, J=9.4, NH), 6.47, 6.17 (2×br s, 2×1H, imide NHs), 5.40 (br d, 1H, J=9.4, H1$^I$), 5.40-4.90 (m, 16H), 4.52 (dd, 1H, J=4.9, 7.5, biotin-H4), 4.36-3.72 (m, 20H), 3.25-3.12 (m, 3H), 2.91 (dd, 1H, J=5.0, 13.0, biotin-H5A), 2.75 (d, 1H, J=12.9, biotin-H5B), 2.27-1.96 (m, 52H), 1.82-1.29 (m, 12H, alkyl chains).

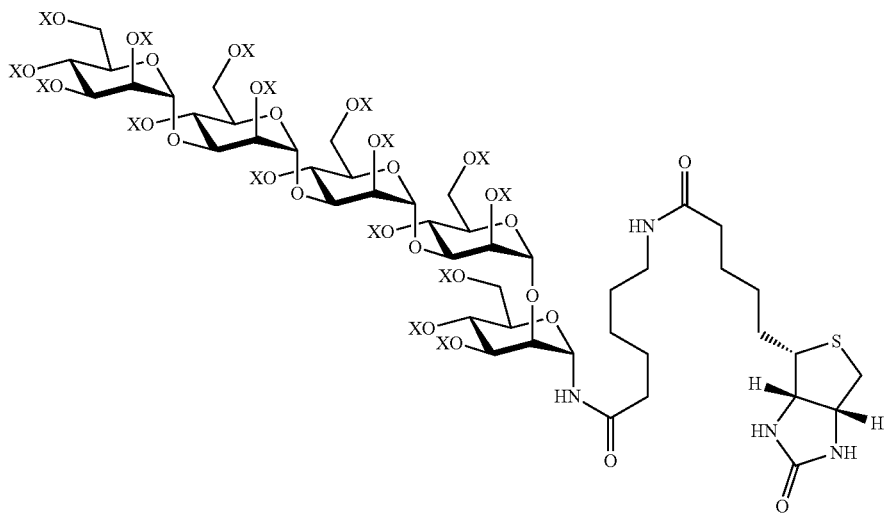

PG503

X = $SO_3Na$ or H

PG503

The peracetate 22 (30 mg, 16.3 μmol) was deacetylated and sulfonated according to the general procedures to yield 28 mg (61% for 2 steps) of PG503 after lyophilisation. $^1$H NMR (400 MHz, $D_2O$, solvent suppressed, affected by amide rotamers) δ 5.60-4.75 (m, 7H, sugar Hs), 4.68 (dd, 1H, J=4.7, 7.2, biotin-H4), 4.60-3.60 (m, 26H, sugar Hs), 4.21 (dd, 1H, J=4.4, 7.2, biotin-H3), 3.33-3.16 (m, 1H, biotin-H2), 3.07-2.97 (m, 3H, biotin-H5A+$CH_2N$), 2.92 (dd, 1H, J=4.9, 13.5, biotin-H$_5$B), 2.33-2.14 (m, 2H, $COCH_2$B), 2.09 (t, 2H, J=7.4, $COCH_2$A), 1.63-1.15 (m, 12H, alkyl chains).

Example 8

PG505

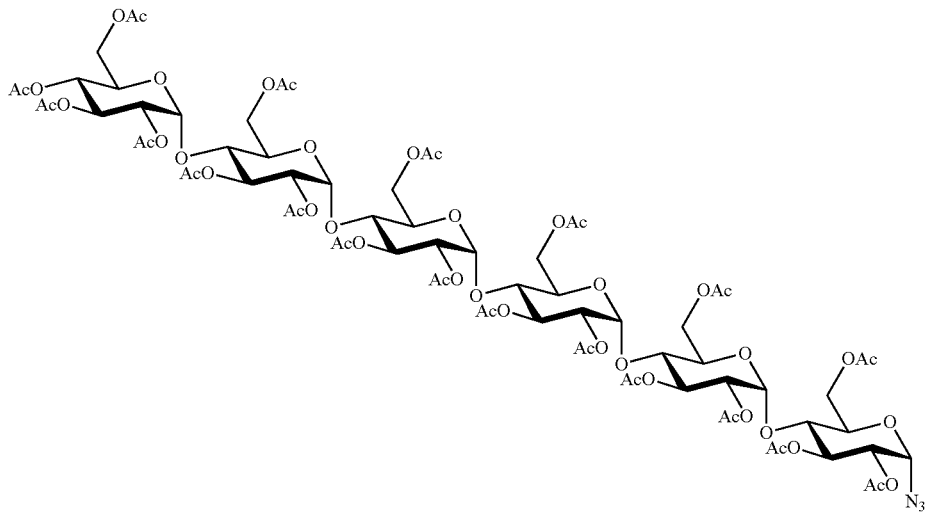

Azide 31.

A solution of maltohexaose peracetate (500 mg, 273 µmol), TMSN₃ (83 mg, 726 µmol) and SnCl₄ (145 µL of 1M in DCM) in anh. DCM (20 mL) was stirred overnight in the dark. Addition quantities of TMSN₃ (50 µL) and SnCl₄ (100 µL of 1M in DCM) were added and stirling was continued in the dark overnight again. Ice and NaHCO₃ (sat. aq.) were added and the mixture was extracted with EtOAc, washed with brine, evaporated and subjected to flash chromatography (10 g silica gel, gradient elution, 75:20 to 80:20 EtOAc:Hx) to yield 488 mg (98%) of azide 31. $^1$H NMR (400 MHz, CDCl₃) δ: 5.30-5.11 (m, 11H), 4.93 (t, 1H, J=9.9), 4.72 (dd, 1H, J=4.0, 10.5), 4.68-4.57 (m, 6H), 4.44-3.67 (m, 23H), 2.09-1.85 (m, 57H). $^{13}$C NMR (100 MHz, CDCl₃) δ: 170.3 (4), 170.3 (1), 170.2 (7), 170.2, 170.1 (4), 170.1 (0), 170.0 (7), 170.0, 169.6, 169.4, 169.3, 169.2 (3), 169.2 (2), 169.1 (7), 169.1 (4), 169.1 (1), 95.5 (0), 95.4 (5), 95.4, 95.3, 87.1, 74.7, 73.9, 73.3, 73.2, 72.2, 71.4, 71.3, 71.2 (4), 71.2 (1), 70.2, 70.1, 69.8, 69.0, 68.8, 68.7, 68.2, 67.7, 62.4, 62.3, 62.1 (8), 62.1 (6), 62.0, 61.1, 30.0, 20.5 (5), 20.5 (3), 20.5 (0), 20.4 (6), 20.3 (3), 20.2 (8), 20.2 (4), 20.2 (2).

PG505

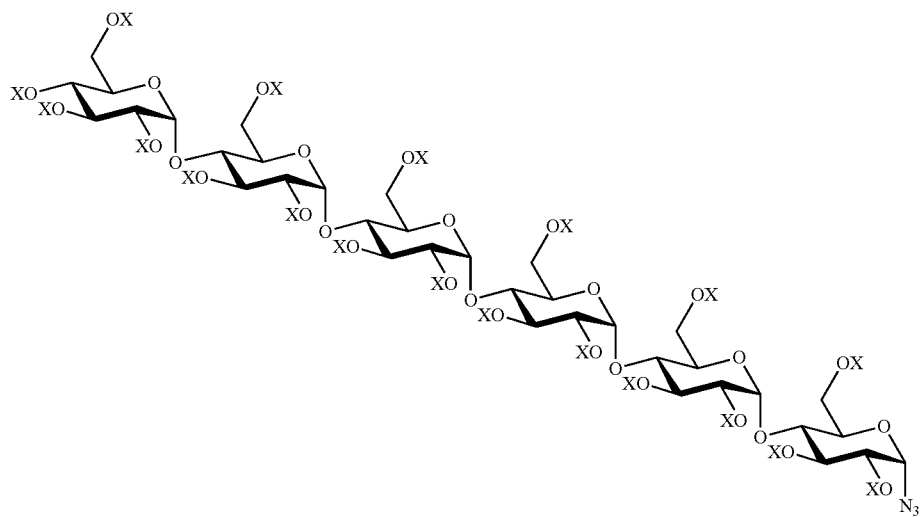

X = SO₃Na or H

PG505

The azide 31 (97 mg, 54 µmol) was deacetylated and sulfonated according to the general procedures to yield 66 mg (41% for 2 steps) of PG505 after lyophilisation. $^1$H NMR (400 MHz, D₂O, solvent suppressed) δ: 3.69-5.78 (m, 42H affected by solvent suppression).

Example 9

PG515

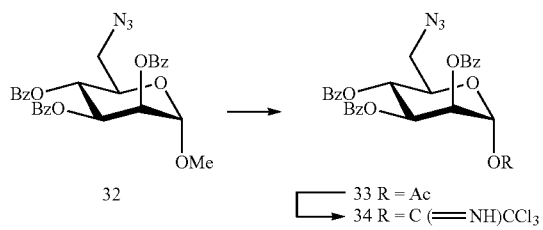

6-Azido-6-deoxy-2,3,4-tri-O-benzoyl-α-D-mannopyranosyl trichloroacetimidate (34)

(A) H$_2$SO$_4$ (0.5 mL) was added to a cooled (0° solution of the methyl glycoside (32) [29] (1.52 g, 2.9 mmol) and Ac$_2$O (10 mL) in AcOH (5 mL) and the combined mixture stirred (0°→r.t., o/n). NaOAc (1.0 g) was added portionwise until pH>5.0 and then the mixture was treated with MeOH (3 mL). The mixture was filtered and the solvent evaporated and co-evaporated (toluene) prior to workup (EtOAc) and RSF (10-20% EtOAc/hexane) to yield presumably the acetate (33) as a colourless foam (1.12 g, 70%).

(B) Hydrazine acetate (196 mg, 2.13 mmol) was added to a stirred solution of the acetate (33) (1.08 g, 1.94 mmol) in DMF (10 mL) and the combined mixture heated (55°, 15 min). The mixture was poured onto saturated NaCl and extracted (EtOAc). The organic layer was evaporated and subjected to RSF (10-30% EtOAc/hexane) to yield a colourless oil (888 mg). This residue was co-evaporated (2×100 mL CH$_3$CN) and used in the next reaction without further purification or characterisation.

(C) DBU (3 drops) was added to a solution of the crude product from (B) (above) (888 mg) and Cl$_3$CN (2.0 mL, 20 mmol) in 1,2-DCE (8 mL) and the combined mixture stirred (0°→r.t., 1 h). The mixture was filtered, the solvent evaporated and the residue subjected to FC (10-30% EtOAc/hexane) to yield the imidate (34) as a colourless oil (777 mg, 61%, 2 steps). $^1$H NMR (400 MHz, CDCl$_3$) δ 8.88 (br s, 1H, NH), 8.10-7.22 (m, 15H, ArH), 6.56 (d, 1H, J$_{1,2}$ 2.0 Hz, H1), 5.99 (dd, 1H, J$_{3,4-4,5}$ 9.6 Hz, H4), 5.94-5.88 (m, 2H, H2,3), 4.44 (ddd, 1H, J$_{5,6}$ 2.8, 5.6 Hz, H5), 3.54 (dd, 1H, J$_{6,6}$ 13.6 Hz, H6), 3.47 (dd, 1H, H6). $^{13}$C NMR (100 MHz, CDCl$_3$) δ 165.61, 165.37, 159.95, 134.00, 133.92, 133.58, 130.25, 130.05, 129.12, 129.04, 128.97, 128.91, 128.76, 128.74, 128.57, 94.62, 73.03, 69.69, 68.90, 67.05, 51.06.

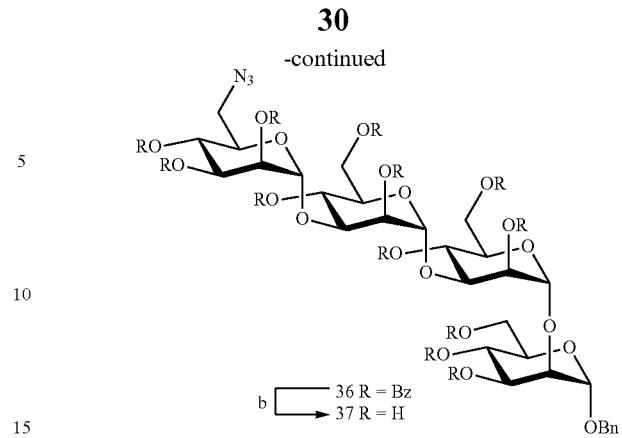

Benzyl (6-azido-6-deoxy-α-D-mannopyranosyl)-(1→3)-(α-D-mannopyranosyl)-(1→3)-(α-D-mannopyranosyl)-(1→2)-(α-D-mannopyranoside)(37)

(A) A mixture of the imidate (34) (93 mg, 141 μmol), the alcohol (35) (90 mg, 94.1 μmol) and mol. sieves (50 mg of 3 Å powder) in 1,2-DCE (3 mL) was treated with TMSOTf (10 μL, 55.1 μmol) and the combined mixture stirred (0°→r.t, 20 min). Et$_3$N (100 μL) was introduced, the mixture was filtered and the solvent was evaporated. The residue subjected to FC (10-40% EtOAc/hexane) to yield the azide (36) as a colourless oil (68 mg, 57%). $^1$H NMR (400 MHz, CDCl$_3$) δ 8.80-7.12 (m, 65H, ArH), 6.01 (dd, 1H, J$_{3,4-4,5}$ 9.9 Hz, H4$^{III}$), 5.96 (dd, 1H, J$_{3,4-4,5}$ 9.9 Hz, H4$^I$), 5.92 (dd, 1H, J$_{3,4-4,5}$ 9.6 Hz, H4$^{II}$), 5.83 (dd, 1H, J$_{2,3}$ 3.3 Hz, H3$^I$), 5.79 (dd, 1H, J$_{1,2}$ 2.0, J$_{2,3}$ 3.3 Hz, H2$^{II}$), 5.70 (dd, 1H, J$_{3,4-4,5}$ 9.9 Hz, H4$^{IV}$), 5.50 (dd, 1H, J$_{2,3}$ 3.3 Hz, H3$^{IV}$), 5.36 (d, 1H, J$_{1,2}$ 1.7 Hz, H1$^{III}$), 5.29 (dd, 1H, J$_{2,3}$ 3.0 Hz, H2$^{III}$), 5.23 (d, 1H, H1$^{II}$), 5.18 (dd, 1H, J$_{1,2}$ 1.9 Hz, H2$^{IV}$), 5.16 (d, 1H, J$_{1,2}$ 1.6 Hz, H1$^I$), 4.87 (d, 1H, H1$^{IV}$), 4.72-4.24 (m, 14H,H2$^I$,H3$^{II,III}$,H5$^{I-III}$,H6$^{I-III}$), 3.99 (ddd, 1H, J$_{5,6}$ 2.9, 3.4 Hz, H5$^{IV}$), 3.02 (dd, 1H, J$_{6,6}$ 13.5 Hz, H6$^{IV}$), 2.83 (dd, 1H, H6$^{IV}$).

(B) The benzoate (36) (63 mg, 31 μmol) was transesterified according the general procedure and chromatography (C18, 0-10% MeOH/H$_2$O) of the residue to yield the tetrasaccharide (37) as a colourless glass (15 mg, 62%). $^1$H NMR (400 MHz, MeOD) δ 7.34-7.22 (m, 5H, ArH), 5.12 (d, 1H, J$_{1,2}$ 1.5 Hz, H1a), 5.09 (d, 1H, J$_{1,2}$ 1.7 Hz, H1b), 5.07 (d, 1H, J$_{1,2}$ 1.6 Hz, H1c), 4.92 (d, 1H, J$_{1,2}$ 1.9 Hz, H1d), 4.71, 4.48 (AB of AB quartet, J 11.7 Hz, CH$_2$Ph), 4.14 (dd, 1H, J$_{2,3}$ 3.0 Hz, H2a), 4.19 (dd, 1H, J$_{2,3}$ 3.2 Hz, H2b), 3.96 (dd, 1H, J$_{2,3}$ 3.4 Hz, H2c), 3.94 (dd, 1H, J$_{3,4}$ 9.4 Hz, H3b), 3.88-3.52 (m, 19H,H2d, H3a,c,d,H4a-d,H5a-d,H6a-d), 3.44 (dd, 1H, J$_{5,6}$ 6.3, J$_{6,6}$ 10.1 Hz, H6$^{IV}$).

PG515

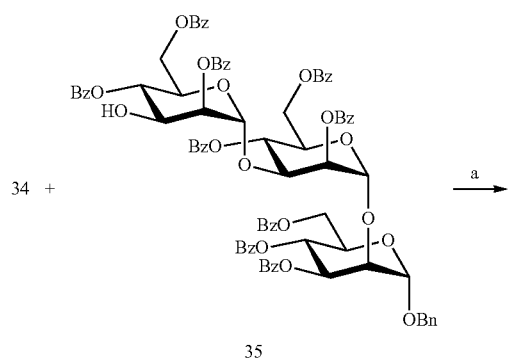

X = SO$_3$Na or H

PG515

The tetrasaccharide 37 (12 mg, 15.3 μmol) was sulfonated according to the general procedures to yield 14 mg (38% for 2 steps) of PG515 after lyophilisation. $^1$H NMR (500 MHz, D$_2$O) δ 7.47-7.37 (m, 1H, ArH), 5.45-4.02 (m, 29H, C1$^{I-IV}$, 2$^{I-IV}$,3$^{I-IV}$,4$^{I-IV}$,5$^{I-IV}$,6a$^{I-IV}$,6b$^{I-III}$, CH$_2$Ph), 3.69-3.67 (m, 1H, H6b$^{IV}$).

Example 10

PG509

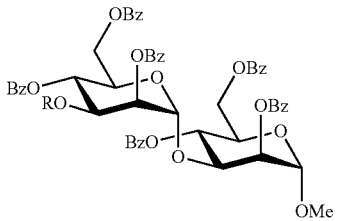

38 R = allyl
39 R = H

Methyl 3-O-(2,4,6-Tri-O-benzoyl-α-D-mannopyranosyl)-2,4,6-tri-O-benzoyl-α-D-mannopyranoside (39)

(A) A mixture of 3-O-allyl-2,4,6-tri-O-benzoyl-α-D-mannopyranosyl trichloro-acetamidate [26] (410 mg, 0.57 mmol) and methyl 2,4,6-tri-O-benzoyl-α-D-mannopyranoside [26] (300 mg, 0.51 mmol) in 1,2-DCE (6 mL) in the presence of mol. sieves (700 mg of 3 Å powder) was treated with TMSOTf (30 μL, 0.17 mmol) and the combined mixture stirred (0°→r.t, 30 min). Et$_3$N (100 μL) was introduced, the mixture was filtered and the solvent was evaporated. The residue subjected to FC (10-50% EtOAc/hexane) to yield, presumably, disaccharide 38 as a colourless oil.

(B) PdCl$_2$ (40 mg) was added to a solution of the product from (A) in MeOH (10 mL) and 1,2-DCE (10 mL) and the combined mixture was heated (70°, 40 min). The solvents were evaporated and the residue subjected to FC (10-50% EtOAc/hexanes) to yield the alcohol (39) as a colourless oil (316 mg, 68%, 2 steps). The $^1$H and $^{13}$C NMR (CDCl$_3$) spectra were similar to those already reported in the literature [26].

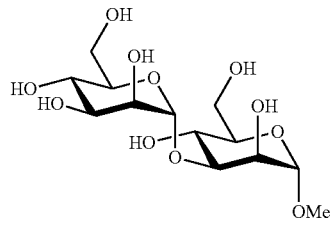

40

Methyl (α-D-mannopyranosyl)-(1→3)-(α-D-mannopyranoside)(40)

The alcohol (39) (10 mg, 0.10 mmol) was transesterified according the general procedure to yield the disaccharide (40) as a colourless oil (3 mg, 85%), identical by NMR to that reported in the literature [30,31].

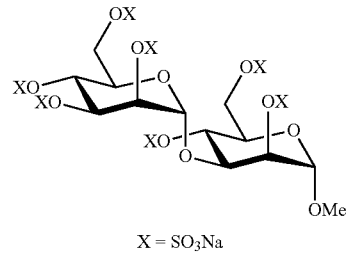

X = SO$_3$Na

PG509.

The disaccharide 40 (25 mg, 70 μmol) was sulfonated according to the general procedures to yield 27 mg (36%) of PG509 after lyophilisation. $^1$H NMR (400 MHz, D$_2$O) δ 5.26 (d, 1H, J$_{1,2}$ 1.8 Hz; H1$^{II}$), 4.98 (dd, 1H, J$_{2,3}$ 2.4 Hz; H2"), 4.87 (d, 1H, J$_{1,2}$ 1.9 Hz; H1$^{I}$), 4.60-4.55 (m, 1H; H3$^{II}$), 4.53 (dd, 1H, J$_{2,3}$ 2.3 Hz; H2$^{1}$), 4.41-4.19 (m, 5H; H4$^{I}$,4$^{II}$,6a$^{I}$,6a$^{II}$,6b$^{II}$), 4.15 (dd, 1H, J$_{3,4}$ 9.3 Hz; H3$^{I}$), 4.06-3.91 (m, 3H; H5$^{I}$,5$^{II}$,6b$^{I}$), 3.29 (s, 3H; OCH$_3$).

Example 11

PG508

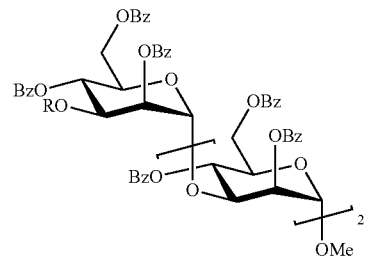

41 R = allyl
42 R = H

Methyl 3-O-[3-O-(2,4,6-Tri-O-benzoyl-α-D-mannopyranosyl)-2,4,6-tri-O-benzoyl-α-D-mannopyranosyl]-2,4,6-tri-O-benzoyl-α-D-mannopyranoside (42)

(A) A mixture of 3-O-allyl-2,4,6-tri-O-benzoyl-α-D-mannopyranosyl trichloro-acetamidate (269 mg, 0.37 mmol) and the alcohol (39) (306 mg, 0.31 mmol) in 1,2-DCE (5 mL) in the presence of mol. sieves (100 mg of 3 Å powder) was treated with TMSOTf (20 μL, 0.11 mmol) and the combined mixture stirred (0°→r.t, 30 min). Et$_3$N (100 μL) was introduced, the mixture was filtered and the solvent was evaporated. The residue subjected to FC (10-50% EtOAc/hexane) to yield, presumably, the trisaccharide 41 as a colourless oil.

(B) PdCl$_2$ (40 mg) was added to a solution of the product from (A) in MeOH (10 mL) and 1,2-DCE (10 mL) and the combined mixture was heated (70°, 40 min). The solvents were evaporated and the residue subjected to FC (10-50% EtOAc/hexanes) to yield the alcohol (42) as a colourless oil (316 g, 70%, 2 steps). $^1$H NMR (400 MHz, CDCl$_3$) δ 8.14-7.22 (m, 45H, ArH), 6.63 (dd, 1H, J$_{1III,2III}$ 1.8, J$_{2III,3III}$ 3.3 Hz, H2$^{III}$), 5.94 (dd, 1H, J$_{3III,4III}$ 10.0, J$_{4III,5III}$ 10.0 Hz, H4$^{III}$), 5.84 (dd, 1H, J$_{3II,4II}$ 9.9, J$_{4II,5II}$ 9.9 Hz, H4$^{II}$), 5.48 (dd, 1H, J$_{3I,4I}$ 9.8, J$_{4I,5I}$ 9.8 Hz, H4$^{I}$), 5.26 (d, 1H, J$_{1,2I}$ 1.9 Hz, H1$^{I}$), 5.22 (dd, 1H, J$_{1II,2II}$ 2.1, J$_{2II,3II}$ 3.0 Hz, H2$^{II}$), 4.91 (d, 1H, H1$^{III}$), 4.90 (dd, 1H, J$_{2I,3I}$ 3.2 Hz, H2$^{I}$), 4.86 (dd, 1H, J$_{1II,2II}$ 1.7 Hz, H1$^{II}$). 4.67-4.63 (, 12H, H3$^{I}$,3$^{II}$,3$^{III}$,5$^{I}$,5$^{II}$,5$^{III}$,6$^{I}$,6$^{II}$, 6$^{III}$). $^{13}$C NMR (100 MHz, CDCl$_3$) δ 166.49, 166.38, 166.25, 166.07, 165.94, 165.77, 165.63, 165.19, 165.15, 133.80, 133.60, 133.61, 133.58, 133.52, 133.06, 130.22, 130.16, 130.09, 130.05, 130.16, 129.97, 129.9, 129.88, 129.84, 129.51, 129.17, 129.01, 128.85, 128.63, 128.53, 128.5, 128.46, 99.35, 99.24, 98.73, 76.48, 76.12, 72.45, 71.77, 71.64, 69.93, 69.7, 69.01, 68.86, 68.6, 68.53, 67.82, 63.17, 62.79, 62.41, 55.66; ESMS: m/z 1373.4 [M−Bz+H+Na]$^+$, 1269.4 [M−2Bz+2H+Na]$^+$.

43

Methyl (α-D-mannopyranosyl)-(1→3)-(α-D-mannopyrano-syl)-(1→3)-(α-D-mannopyranoside) (43)

The alcohol (42) (115 mg, 0.79 mmol) was transesterified according the general procedure to yield the trisaccharide (43) as a colourless oil (35 mg, 86%), identical by NMR to that reported in the literature [32]. HRMS: m/z 519.1862 [M+H]$^+$, 541.1646 [M+Na]$^+$.

PG508

X = SO$_3$Na or H

PG508.

The trisaccharide 43 (25 mg, 49 μmol) was sulfonated according to the general procedures to yield 36 mg (49%) of PG508 after lyophilisation. $^1$H NMR (400 MHz, D$_2$O) δ 5.26 (d, 1H, J$_{1,2}$ 1.9 Hz; H1$^{III}$), 5.22 (d, 1H, J$_{1,2}$ 1.8 Hz; H1$^{II}$), 5.04 (dd, 1H, J$_{2,3}$ 2.4 Hz; H2$^{III}$), 4.89 (d, 1H, J$_{1,2}$ 1.6 Hz; H1$^I$), 4.76-4.75 (m, 1H; H2″), 4.60-4.55 (m, 1H; H3$^{III}$), 4.55 (dd, 1H, J$_{2,3}$ 3.1 Hz; H2$^1$), 4.50 (dd, 1H, J$_{3,4}$ 9.6, J$_{4,5}$ 9.7 Hz; H4$^{III}$), 4.41-4.12, 4.04-3.91 (m, 12H; H3$^{II}$,4$^I$,4$^{II}$,5$^{I-III}$,6a$^{I-III}$,6b$^{I-III}$), 4.10 (dd, 1H, J$_{3,4}$ 9.5 Hz; H3$^I$), 3.29 (s, 3H; OCH$_3$).

Example 12

PG512

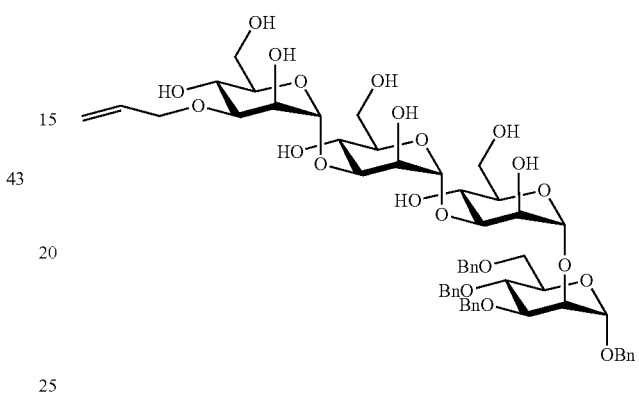

44

Benzyl (3-O-Allyl-α-D-mannopyranosyl)-(1→3)-(α-D-mannopyranosyl)-(1→3)-(α-D-mannopyranosyl)-(1→2)-(3,4,6-tri-O-benzyl-α-D-mannopyranoside) (44)

Sodium (small piece) was added to the nonabenzoate (28) (115 mg, 0.79 mmol) in MeOH (6 mL) and the combined mixture stirred (r.t., o/n). The mixture was neutralised (Dowex 50×8, H$^+$), filtered and the filtrate concentrated and subjected to FC (0-10% MeOH/CH$_2$Cl$_2$) to yield the tetrabenzyl ether (44) as a colourless oil (89 mg, 64%). $^1$H NMR (CD$_3$OD) δ 7.33-7.13 (m, 20H, ArH), 6.02-5.92 (m, 1H, CH=CH$_2$), 5.32-5.27, 5.11-5.09 (2 m, 2H, CH=CH$_2$), 5.10 (d, 1H, J$_{1,2}$ 1.4 Hz, H1a), 5.09 (d, 1H, J$_{1,2}$ 1.5 Hz, H1b), 5.03 (d, 1H, J$_{1,2}$ 1.2 Hz, H1c), 4.97 (d, 1H, J$_{1,2}$ 1.4 Hz, H1d), 4.74, 4.49 (2d, AB of ABq, J$_{H,H}$ 10.9 Hz, PhCH$_2$-a), 4.67, 4.48 (2d, AB of ABq, J$_{H,H}$ 11.8 Hz, PhCH$_2$-b), 4.65, 4.58 (2d, AB of ABq, J$_{H,H}$ 11.6 Hz, PhCH$_2$-c), 4.57, 4.51 (2d, AB of ABq, J$_{H,H}$ 12.4 Hz, PhCH$_2$-d), 4.21-3.62 (m, 26H, H2$^{I-IV}$,3$^{I-IV}$,4$^{I-IV}$,5$^{I-IV}$,6a$^{I-IV}$,6b$^{I-IV}$, OCH$_2$CH=).

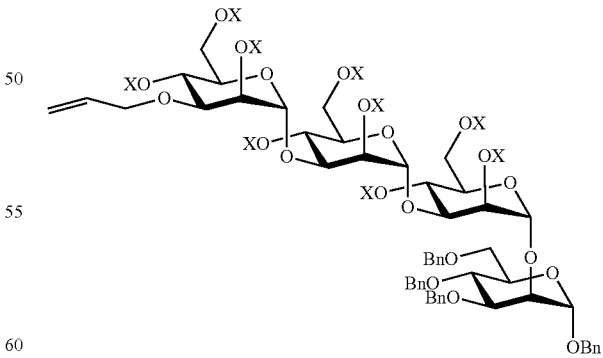

PG512

X = SO$_3$Na or H

PG512

The tetrasaccharide 44 (23 mg, 21.5 μmol) was sulfonated according to the general procedures to yield PG512 as a colourless powder (26 mg, 61%). $^1$H NMR (400 MHz, D$_2$O)

δ 7.32-7.18, 7.00-6.98 (2 m, 20H, ArH), 5.88-5.78 (m, 1H, CH=CH$_2$), 5.30-5.23, 5.08-5.04, 4.91-4.90, 4.83-4.82, 4.71-4.08, 4.00-3.89, 3.73-3.70, 3.62-3.45 (8 m, 40H, CH=CH$_2$, OCH$_2$CH, H1-6$^{I-IV}$, PhCH$_2^{I-IV}$).

Example 13

PG513

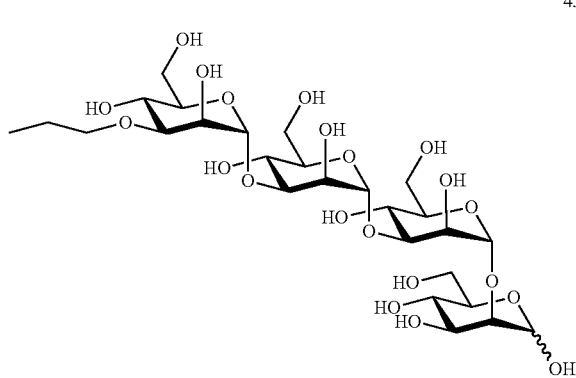

A mixture of the tetrabenzyl ether (44) (62 mg, 50 μmmol) and Pd(OH)$_2$ (10 mg of 10% on C) in THF (1 mL) and H$_2$O (1 mL) was stirred under H$_2$ (100 p.s.i.) (r.t., o/n). The mixture was filtered, concentrated and subjected to FC (SiO$_2$; H$_2$O) to yield the propyl ether (45) as a colourless glass (32 mg, 73%). $^1$H NMR (D$_2$O) δ 5.22 (br s, 1H, H1a), 5.00 (d, 1H, J$_{1,2}$ 1.7 Hz, H1b), 4.97 (d, 1H, J$_{1,2}$ 1.6 Hz, H1c), 4.87 (d, 1H, J$_{1,2}$ 1.8 Hz, Hid), 4.11-4.07, 3.91-3.35 (2 m, 26H, H2$^{I-IV}$,3$^{I-IV}$,4$^{I-IV}$, 5$^{I-IV}$,6a$^{I-IV}$,6b$^{I-IV}$, OCH$_2$), 1.50-1.42 (m, 2H, CH$_2$CH$_3$), 0.76 (t, 3H, J$_{H,H}$ 7.2 Hz, CH$_2$CH$_3$).

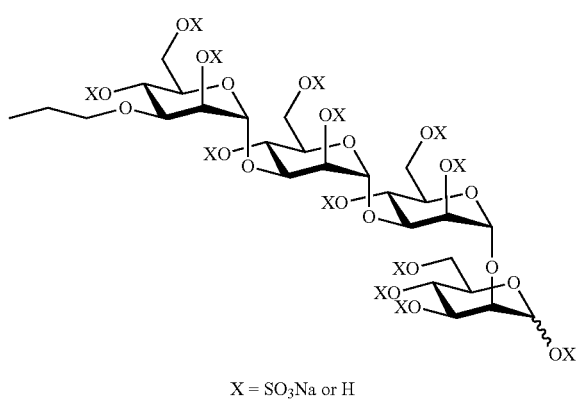

PG513

X = SO$_3$Na or H

PG513

The tetrasaccharide 45 (21 mg, 29.6 μmol) was sulfonated according to the general procedures to yield PG513 as a colourless powder (29 mg, 34%). $^1$H NMR (D$_2$O) δ 5.61 (d, 1H, J$_{1,2}$ 2.3 Hz; H1a), 5.61 (br s, 1H; H1b), 5.32 (d, 1H, J$_{1,2}$ 1.8 Hz; H1c), 5.26 (d, 1H, J$_{1,2}$ 2.0 Hz; Hid), 4.90-4.88, 4.77-4.31, 4.23-4.04, 3.98-3.81, 3.57-3.51, 3.41-3.36 (6 m, 26H, OCH$_2$CH$_2$, H2-6$^{I-IV}$), 1.48-1.39 (m, 1H; CH$_2$CH$_3$), 0.76 (dd, 1H, J$_{H,H}$ 7.4 Hz; CH$_2$CH$_3$).

Example 14

PG510

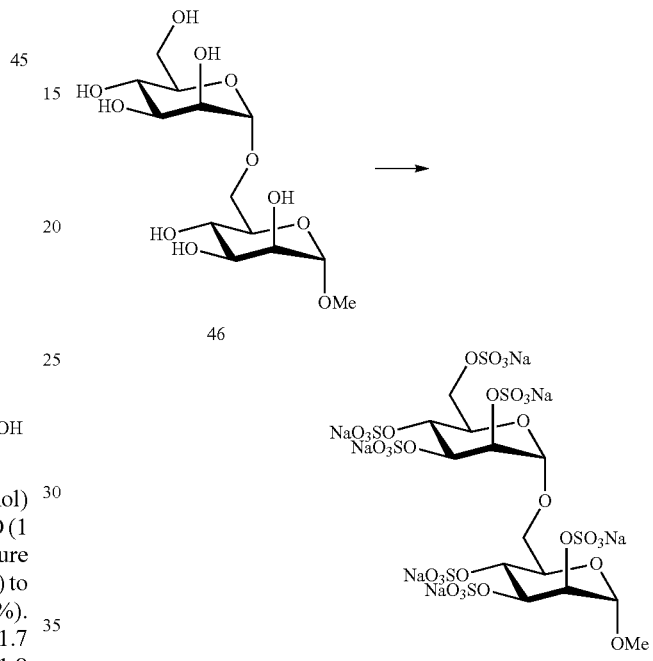

The polyol 46 [31] (22 mg, 61.7 μmol) was sulfonated according to the general procedure to yield PG510 as a colourless powder (46 mg, 70%). $^1$H NMR (D$_2$O) δ 5.10 (d, 1H, J$_{1,2}$ 2.0 Hz; H1$^{II}$), 4.90 (d, 1H, J$_{1,2}$ 2.0 Hz; H1$^I$), 4.78 (dd, 1H, J$_{2,3}$ 3.0 Hz; H2$^{II}$), 4.73 (dd, 1H, J$_{2,3}$ 3.1 Hz; H2$^I$), 4.64-4.40 (m, 1H; H3$^{II}$), 4.52 (dd, 1H, J$_{3,4}$ 9.5 Hz; H3$^I$), 4.33-4.30 (m, 2H; H4$^{II}$,6a$^{II}$), 4.22 (dd, 1H, J$_{4,5}$ 9.7 Hz; H4$^I$), 4.12-4.04 (m, 2H; H5$^{II}$,6b$^{II}$), 3.96-3.90 (m, 2H; H5$^I$,6a$^I$), 3.76 (dd, 1H, J$_{5,6b}$ 8.6, J$_{6a,6b}$ 11.3 Hz; H6b$^I$), 3.31 (s, 3H; OCH$_3$).

Example 15

PG511

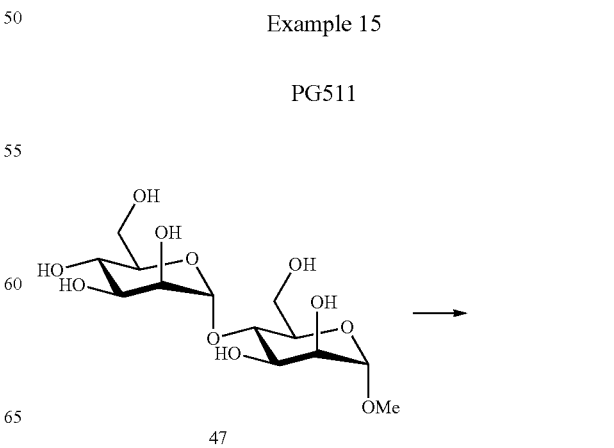

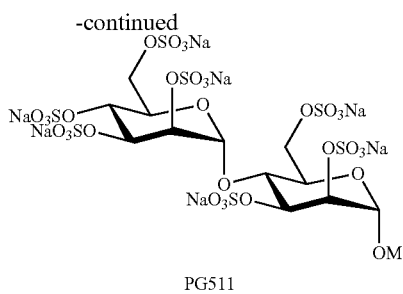

PG511

The polyol 47 [31] (20 mg, 56 µmol) was sulfonated according to the general procedure to yield PG511 as a colourless powder (29 mg, 48%). $^1$H NMR (D$_2$O) δ 5.36 (d, 1H, J$_{1,2}$ 2.2 Hz; H1$^{II}$), 4.90 (br s, 1H; H2$^{II}$), 4.87 (d, 1H, J$_{1,2}$ 2.1 Hz; H1$^{I}$), 4.74 (dd, 1H, J$_{2,3}$ 3.0 Hz; H2$^{II}$), 4.58-4.40, 4.29-4.10, 3.88-3.85 (3 m, 10H, H3-6$^{I,II}$), 3.30 (s, 3H; OCH$_3$).

Example 16

PG514

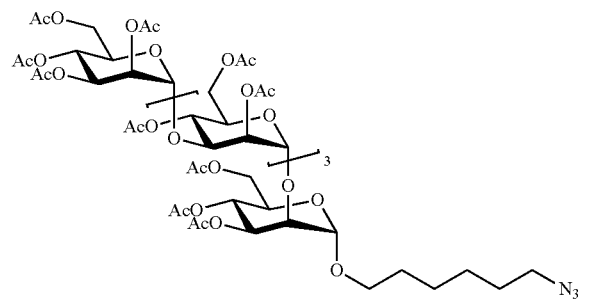

18

Azide 18

(A) Boron trifluoride diethyl etherate (257 mg, 1.81 mmol) was slowly added to a solution of the peracetate 12 (700 mg, 0.453 mmol) and 6-bromo-1-hexanol (492.7 mg, 2.721 mmol) in DCE (20 mL, 3 Å molecular sieves) and the mixture was stirred under argon at 60° C. for 72 h. The solution was cooled, neutralised with Et$_3$N, diluted with DCM (30 mL), washed with sat. NaHCO$_3$, dried (MgSO$_4$) and subjected to flash chromatography (silica, gradient elution, 40:60 to 100:0 EtOAc:Hx) to afford 340 mg (0.204 mmol, 45.0%) of the 6-bromohexyl glycoside. $^1$H NMR (400 MHz, CDCl$_3$) δ: 5.25-5.08 (m, 8H), 4.98-4.81 (m, 8H), 4.25-3.70 (m, 19H), 3.607 (dt, 1H, J=9.553, J=6.635, OCH$_2$A), 3.354 (dt, 1H, J=9.641, J=6.637, OCH$_2$B), 3.33 (t, 2H, J=6.700, CH$_2$Br), 2.104, 2.096, 2.09, 2.06, 2.043, 2.038, 2.036, 2.033, 2.029, 2.02, 2.01, 1.97, 1.95, 1.94 and 1.90 (16×S, 48H, OAc), 1.85-1.74 (m, 2H, CH$_2$), 1.59-1.46 (m, 2H, CH$_2$), 1.44-1.35 (m, 2H, CH$_2$), 1.35-1.25 (m, 2H, CH$_2$); $^{13}$C NMR (CDCl$_3$, 100 MHz): 170.42, 170.41, 170.39, 170.28, 170.16, 170.07, 169.96, 169.94, 169.83, 169.77, 169.58, 169.52, 169.45, 169.36, 169.25 (19×CO), 99.10, 98.83, 98.75, 98.01 (sugar-C1), 76.96, 75.00, 74.83, 74.75, 70.96, 70.82, 70.70, 70.08, 69.49, 69.28, 69.16, 68.24, 68.17, 68.04, 67.20, 66.65, 66.60, 66.09, 65.44, 62.41, 62.31, 61.86, and 61.54 (sugar carbons excluding sugar-C1 and bromohexyl-CH$_2$O), 33.49, 32.32, 29.43, 28.92, 27.59, 25.12 (6x bromohexyl-CH$_2$), 20.73, 20.71, 20.68, 20.62, 20.56, 20.47, 20.44, 20.41, (Ac—CH$_3$), 13.85 (CH$_2$Br).

(B) A solution of 6-bromohexyl glycoside from (A) (340 mg, 0.204 mmol) and sodium azide (66 mg, 1.02 mmol) in DMF (4 mL) was heated at 100° C. for 48 h. TLC analysis of the crude mixture indicated no change. Tetrabutylammonium idiode (20 mg) was then added and the mixture allowed to react for a further 48 h. The crude mixture was cooled and subjected to flash chromatography (0:100 to 5:95 DCM:MeOH) to afford 21.1 mg (0.013 mmol, 6.4%) of azide 18.

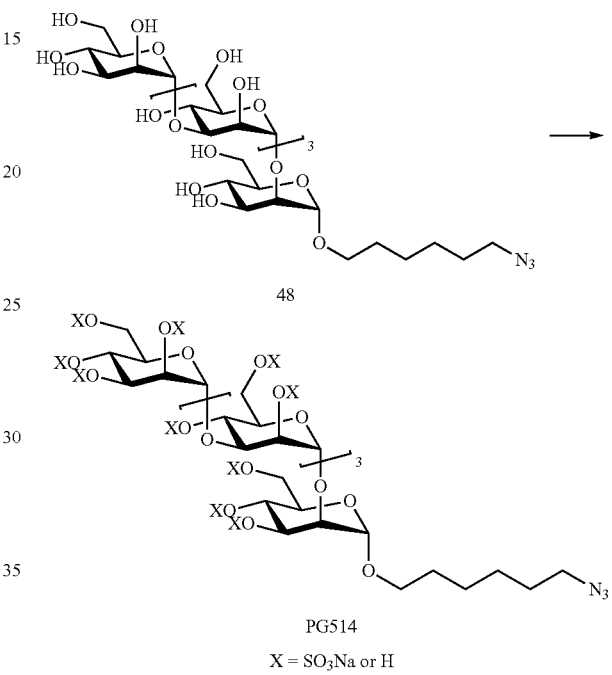

X = SO$_3$Na or H

PG514

(A) The azide 18 (21.1 mg, 0.013 mmol) was deacetylated under standard Zemplén conditions (2 mL MeOH) to afford 12.6 mg (0.013 mmol, 102%) of polyol 48.

(B) The polyol 48 (12.6 mg, 13.2 µmol) was treated with SO$_3$.trimethylamine according to the general sulfation procedure to yield PG514 as a colourless powder (18.4 mg, 54%). $^1$H NMR (D$_2$O, 400 MHz): 5.40-4.69 (m, 8 H), 4.68-3.41 (m, 27H), 3.22 (t, 2H, J=6.5), 1.51 (br s, 5H), 1.29 (br s, 5H).

Biological Testing of Compounds

Growth Factor Binding Assays

Binding affinities of ligands for the growth factors FGF-1, FGF-2 and VEGF were measured using a surface plasmon resonance (SPR) based solution affinity assay. The principle of the assay is that heparin immobilised on a sensorchip surface distinguishes between free and bound growth factor in an equilibrated solution of the growth factor and a ligand. Upon injection of the solution, the free growth factor binds to the immobilised heparin, is detected as an increase in the SPR response and its concentration thus determined. A decrease in the free growth factor concentration as a function of the ligand concentration allows for the calculation of the dissociation constant, K$_d$. It is important to note that ligand binding to the growth factors can only be detected when the interaction involves the HS binding site, thus eliminating the chance of evaluating non-specific binding to other sites on the protein. A 1:1 stoichiometry has been assumed for all protein:ligand interactions.

For the testing of growth factor binding activity, heparin-coated sensorchips were used. Their preparation, via immobilisation of biotinylated BSA-heparin on a streptavidin-coated sensorchip, has been described.[5] Heparin has also been immobilised via aldehyde coupling using either adipic acid dihydrazide or 1,4-diaminobutane. For each $K_d$ measurement, solutions were prepared containing a fixed concentration of protein and varying concentrations of the ligand in buffer. Ligands binding to FGF-1 and VEGF were measured in HBS-EP buffer (10 mM HEPES, pH 7.4, 150 mM NaCl, 3.0 mM EDTA and 0.005% (v/v) polysorbate 20), while binding to FGF-2 was measured in HBS-EP buffer containing 0.3 M NaCl.[5] Prior to injection, samples were maintained at 4° C. to maximise protein stability. For each assay mixture, 50-200 μL of solution was injected at 5-40 μL/min and the relative binding response measured. All surface binding experiments were performed at 25° C. The surface was regenerated by injection of 40 μL of 4M NaCl at 40 μL/min, followed by injection of 40 μL of buffer at 40 μL/min.

Sensorgram data were analysed using the BIAevaluation software (BIAcore). Background sensorgrams were subtracted from experimental sensorgrams to produce curves of specific binding, and baselines were subsequently adjusted to zero for all curves. Standard curves relating the relative response value to the injected protein concentration are linear, indicating that the binding response is proportional to the protein concentration, and thus suggesting that the binding experiments were conducted under mass transport conditions.[34] Therefore, the relative binding response for each injection can be converted to free protein concentration using the equation.

$$[P] = \frac{r}{r_m}[P]_{total}$$

where $r$ is the relative binding response and $r_m$ is the maximal binding response.

Binding equilibria established in solution prior to injection were assumed to be of 1:1 stoichiometry. Therefore, for the equilibrium, $$P + L \rightleftharpoons P \cdot L$$

where P corresponds to the growth factor protein, L is the ligand, and P·L is the protein:ligand complex, the equilibrium equation is $$K_d = \frac{[P][L]}{[P \cdot L]}$$

and the binding equation[5] can be expressed as $$[P] = [P]_{total} - \frac{(K_d + [L]_{total} + [P]_{total})}{2} + \sqrt{\frac{(K_d + [L]_{total} + [P]_{total})^2}{4} - [L]_{total}[P]_{total}}$$

The $K_d$ values given are the values fit, using the binding equation, to a plot of [P] versus $[L]_{total}$. Where $K_d$ values were measured in duplicate, the values represent the average of the duplicate measurements. It has been shown that GAG mimetics that bind tightly to these growth factors, e.g., PI-88, elicit a biological response in vivo.[5]

Heparanase Inhibition Assays

The heparanase assays were performed using a Microcon ultrafiltration assay. The assays rely on the principle of physically separating heparan sulfate (HS) that has been digested by heparanase from native HS to determine heparanase activity. The assay uses ultrafiltration devices (Microcon YM-10) to separate the smaller heparanase-cleaved HS fragments from native HS.

A reaction was set up with a volume of 90 μL, 40 mM acetate buffer (pH 5.0)

0.1 mg/mL BSA 90 ng heparanase 2.5 μM $^3$H labelled HS various concentrations of inhibitors.

The reactions were set up with all components except the $^3$H labelled HS and allowed to equilibrate for 10 min at 22° C. The assays were then initiated by adding the HS and immediately 20 μL was taken, mixed with 80 μL of 10 mM phosphate (pH 7.0) and the 100 μL transferred to a Microcon YM-10 concentrator which was then centrifuged at approximately 14000 g for 5 min. The solution that passed through the membrane (filtrate) was retained. This sample was considered the time=0 sample. The assays (now 70 μL in volume) were allowed to react at 22° C. for 2.5 h and then the filtration step was repeated for three aliquots of 20 μL from each assay.

The time=0 filtrate and the three 2.5 h filtrate samples were counted for $^3$H. The difference between the time=0 and the averaged 2.5 h samples gave the amount of heparanase activity. All inhibition assays were run with a heparanase standard assay which was identical to the assay composition above except no inhibitor was present and the amount of heparanase inhibition in the other assays determined by comparison with this standard. The $IC_{50}$ for PI-88 in this assay is 0.98 μM.

Antiviral Assays

Monolayer cultures of African green monkey kidney cells [35] and herpes simplex virus (HSV-1) KOS321 strain[36] were used throughout. The antiviral assays on the compounds were performed as described by Nyberg et al.[13] Briefly, the effects of the compounds on the infection of cells by exogenously added virus were tested by mixing serial fivefold dilutions of compound (at 0.032-20 μM) with approximately 200 plaque forming units of the virus. Following incubation of the virus and compound for 10 min at room temperature, the mixture was added to the cells and left on the cell monolayer for 2 h at 37° C. Subsequently, the inoculum was aspirated and replaced with an overlay medium of 1% methylcellulose solution in Eagle's minimum essential medium (EMEM). The viral plaques that developed after incubation of cells for 3 days at 37° C. were stained with 1% crystal violet solution and counted. The effects of the compounds on cell-to-cell spread of HSV-1 were tested by adding serial fivefold dilutions of compound (at 0.032-20 μM) in the serum-free overlay medium to cells after their infection with HSV-1. After incubation of the compound with the cells for 3 days at 37° C., the images of 20 plaques were captured and subjected to area determination using IM500 software (Leica). The results on viral infection of cells and on viral cell-to-cell spread are shown in FIGS. 1A and 1B, respectively, whilst the derived $IC_{50}$ values are presented in Table 1.

Results

The results of the tests as described in the preceding section are presented in Table 1.

TABLE 1

| Compound | $K_d$ aFGF (pM) | $K_d$ bFGF (nM) | $K_d$ VEGF (nM) | Heparanase Inhibition ($IC_{50}$, μM) | HSV-1 Infectivity ($IC_{50}$, μM) | HSV-1 cell-to-cell spread ($IC_{50}$, μM) |
|---|---|---|---|---|---|---|
| PG500 | 120 ± 25 | 86 ± 7 | 1.72 ± 0.19 | 1.83 ± 0.483 | 2 | 1 |
| PG501 | 144 ± 8 | 68.3 ± 2.9 | 1.67 ± 0.11 | 1.64 ± 0.406 | 1 | 0.4 |
| PG502 | 660 ± 40 | 112 ± 9 | 7.1 ± 0.6 | 2.02 ± 0.284 | 7 | 5 |
| PG503 | 390 ± 70 | 84 ± 8 | 7.2 ± 0.6 | 1.85 ± 0.311 | 2 | 3 |
| PG504 | 361 ± 28 | 150 ± 9 | 8.1 ± 0.6 | 6.03 ± 1.05 | Not tested | 11 |
| PG505 | 1960 ± 300 | 137 ± 12 | 4.8 ± 0.4 | 1.04 ± 0.147 | 3 | 6 |
| PG506 | 88 ± 17 | 114 ± 13 | 3.5 ± 0.8 | 2.12 ± 0.152 | 10 | 7 |

Pharmacokinetic Evaluation

Preparation of [$^{35}$S]-labelled Compounds

The polyol precursors for PG500, 501, 503, 504, 506 and PI-88 (2 mg of each) were desiccated under vacuum over $P_2O_5$ for 3 days. Into each vial was syringed 50 μL of a stock solution of 1.77 mg (2.0 mCi) of $^{35}SO_3$.pyridine complex and 2 mg $SO_3.Me_3N$ in 300 μL of anhydrous DMF (Aldrich, redried over freshly ignited 3 A molecular sieves). A further 600 μL of anhydrous DMF was added to the $SO_3$ vial and was distributed to each sample vial. The samples were heated to 60° for 66 hr. $SO_3.Me_3N$ (14 mg in 300 μL anhydrous DMF) was added to each vessel and the resulting solutions were heated to 60° overnight. The vials were cooled to room temperature and stored at −80° C. awaiting purification.

Each sample was quenched by addition of $Na_2CO_3$ (sat. aqu. adjusted to pH 8-9), evaporated to dryness and subjected to SEC (Biogel P2, 2.6×90 cm, flow rate 30 mL/hr, 5 min/fraction). Fractions containing desired material were detected using a G-M counter and DMB test followed by CE. The results are summarized in Table 2.

TABLE 2

Summary of Results for Radio-labelling experiments

| Compound | Quantity Isolated (mg) | Radio-chemical purity | Specific activity (μCi/mg) |
|---|---|---|---|
| PI-88 | 2.8 | 99.0% | 38.01 |
| PG500 | 2.1 | 98.7% | 29.19 |
| PG501 | 1.7 | 98.0% | 6.56 |
| PG503 | 1.0 | 99.2% | 5.49 |
| PG504 | 5.0 | 98.3% | 6.47 |
| PG506 | 3.6 | 99.0% | 26.23 |

Pharmacokinetic Studies

Male Sprague Dawley rats (250-350 g) were used. The animals were allowed free access to food and water before and during the experiments, during which they were maintained unrestrained in metabolism cages. Rats were anaesthetized with isoflurane (Forthane®). A catheter was inserted in the external jugular vein via an incision in the neck, and was passed under the skin to a second incision in the skin of the back (midline vicinity of the scapulae). This was then exteriorized with the protection of a light metal spring. The incision was closed and the spring fixed to the skin with Michel sutures so that the rats had full range of movement. The animals were carefully monitored during recovery (1-4 h).

Stock dosing solutions were prepared by mixing appropriate amounts of unlabelled and radiolabelled drug (dissolved in phosphate-buffered saline) to give a total drug concentration of 1.25 mg/mL. All doses were administered as a bolus intravenous injection of 2.5 mg/kg in a dose volume of 2 mL/kg. The total amount of radioactivity administered to each rat was 0.5-10 μCi. The dose level used in this study is 10-fold lower than the no-effect dose previously established for acute toxicity of PI-88. Blood samples (~250 μL) were collected predose and at 5, 15, 30, 45 min, and 1, 1.5, 2, 4, 8, 12, 24, 36 and 48 h after dosing. The blood samples were immediately centrifuged and the plasma collected. At completion of the experiments, the animals were killed by a lethal overdose of IV pentobarbitone anaesthetic (Nembutal®). Urine was collected from each animal at intervals of 0-12 h, 12-24 h and 24-48 h after dosing. Cage washings (~15 mL of deionised water) were also collected. At the end of the experiment, bladder contents were aspirated from each animal and added to the 24-48 h voidings. Feces were collected over the same time intervals as the urine.

Aliquots of plasma (100 μL), urine and cage washings (500 μL) were transferred directly to 6 mL polypropylene scintillation vials for determination of radioactivity. Feces collected during each time period (from one animal dosed with each compound) were weighed and homogenised in 4 volumes of deionised water using a mechanical homogeniser. Approximately 1 g (accurately weighed) of this slurry was transferred to a 20 mL glass scintillation vial, 2 mL of tissue solubiliser added and the vials capped and incubated at 60° C. for at least 24 h. Radioactivity was measured following mixing of samples with Packard Ultima Gold liquid scintillation counting cocktail (2.0 mL for plasma and dose, 5.0 mL for urine and cage washings, 10 mL for feces). Counting was conducted on a Packard Tr-Carb liquid scintillation counter. Any result less than three times the background was considered less than the lower limit of quantitation not used in calculations. Plasma, urine and cage washings were counted in triplicate within 5 days of collection and were not corrected for radiochemical decay. Feces were processed as a batch at the completion of the study and the counts from these samples were corrected for radiochemical decay. Plasma pharmacokinetic parameters were calculated using PK Solutions 2.0 software (Summit Research Services, Ohio) and are presented in Table 3.

TABLE 3

Pharmacokinetic parameters determined for $^{35}$S-labelled compounds following iv administration to male Sprague Dawley rats

| n | PI-88 4 | PG500 4 | PG501 4 | PG503 4 | PG504 4 | PG506 4 |
|---|---|---|---|---|---|---|
| $C_0$ (µg-eq/mL) | 17.7 ± 2.23 | 20.5 ± 1.3 | 35.6 ± 3.1 | 14.0 ± 0.84 | 30.5 ± 2.3 | 17.1 ± 1.8 |
| $AUC_{0-12\,h}$ (µg-eq/h · mL) | 9.6 ± 1.9 | 12.6 ± 1.2 | 29.7 ± 3.4 | 6.5 ± 0.4[b] | 14.7 ± 1.2 | 6.2 ± 1.0[a] |
| $t_{1/2}$* (h)[c] | 0.83 ± 0.09 | 0.83 ± 0.02 | 1.10 ± 0.09 | 0.79 ± 0.03 | 2.81 ± 0.04 | 0.59 ± 0.01 |
| k* (h$^{-1}$) | 0.844 ± 0.096 | 0.836 ± 0.024 | 0.633 ± 0.053 | 0.879 ± 0.028 | 0.247 ± 0.003 | 1.17 ± 0.024 |
| Cl* (mL/h/kg) | 250 ± 27.6 | 199 ± 13.2 | 83.6 ± 9.1 | 380 ± 24.3[b] | 172 ± 11.8 | 404 ± 59.5 |
| Vd* (mL) | 43.1 ± 1.9 | 38.4 ± 3.8 | 22.9 ± 2.2 | 55.1 ± 2.6 | 24.9 ± 2.9 | 44.5 ± 4.5 |
| Urinary Recovery (% dose) | 59.1 ± 13.1 | 39.3 ± 5.5 | 41.8 ± 1.5 | 80.5 ± 3.9 | 66.5 ± 9.4 | 79.1 ± 3.6 |

*Apparent values.
[a]Calculated over 0-8 h post dose interval only.
[b]Calculated over 0-4 h post dose interval only.
[c]Calculated over the 0.75-4.0 h post dose interval for PI-88, PG500, PG501, PG503 and PG506; calculated over the 4.0-12 h post dose interval for PG504.

The results presented in Table 1 demonstrate that the broad range of compounds embraced by the invention possess heparanase inhibitory activity and have strong affinity for GAG-binding growth factors and can thus serve as modulators of the activity of such factors in a similar manner to PI-88. In addition, the compounds have similar antiviral activity to PI-88. The results presented in Table 3 illustrate that the compounds have altered pharmacokinetic properties compared to PI-88.

The foregoing embodiments are illustrative only of the principles of the invention, and various modifications and changes will readily occur to those skilled in the art. The invention is capable of being practiced and carried out in various ways and in other embodiments. It is also to be understood that the terminology employed herein is for the purpose of description and should not be regarded as limiting.

The term "comprise" and variants of the term such as "comprises" or "comprising" are used herein to denote the inclusion of a stated integer or stated integers but not to exclude any other integer or any other integers, unless in the context or usage an exclusive interpretation of the term is required.

Any reference to publications cited in this specification is not an admission that the disclosures constitute common general knowledge in Australia.

REFERENCES

[1] Parish, C. R.; Freeman, C.; Brown, K. J.; Francis, D. J.; Cowden, W. B. Cancer Res. 1999, 59, 3433.
[2] Parish, C. R.; Cowden, W. B. 6, 143, 730, 2000.
[3] Iversen, P. O.; Sorenson, D. R.; Benestad, H. B. Leukemia 2002, 16, 376.
[4] Ferro, V.; Don, R. Australas. Biotechnol. 2003, 13, 38.
[5] Cochran, S.; Li, C.; Fairweather, J. K.; Kett, W. C.; Coombe, D. R.; Ferro, V. J. Med. Chem. 2003, 46, 4601.
[6] Vlodaysky, I.; Friedmann, Y. J. Clin. Invest. 2001, 108, 341.
[7] Parish, C. R.; Freeman, C.; Hulett, M. D. Biochim. Biophys. Acta 2001, 1471, M99.
[8] Wall, D.; Douglas, S.; Ferro, V.; Cowden, W.; Parish, C. Thromb. Res. 2001, 103, 325.
[9] Demir, M.; Iqbal, O.; Hoppensteadt, D. A.; Piccolo, P.; Ahmad, S.; Schultz, C. L.; Linhardt, R. J.; Fareed, J. Clin. Appl. Thromb. Hemost. 2001, 7, 131.
[10] Hembrough, T. A.; Ruiz, J. F.; Papathanassiu, A. E.; Green, S. J.; Strickland, D. K. J. Biol. Chem. 2001, 276, 12241.
[11] Amirkhosravi, A.; Meyer, T.; Chang, J. Y.; Amaya, M.; Siddiqui, F.; Desai, H.; Francis, J. L. Thromb. Haemost. 2002, 87, 930.
[12] Francis, D. J.; Parish, C. R.; McGarry, M.; Santiago, F. S.; Lowe, H. C.; Brown, K. J.; Bingley, J. A.; Hayward, I. P.; Cowden, W. B.; Campbell, J. H.; Campbell, G. R.; Chesterman, C. N.; Khachigian, L. M. Circ. Res. 2003, 92, e70.
[13] Nyberg, K.; Ekblad, M.; Bergström, T.; Freeman, C.; Parish, C. R.; Ferro, V.; Trybala, E. Antiviral Res. 2004, 63, 15.
[14] Levidiotis, V.; Freeman, C.; Punler, M.; Martinello, P.; Creese, B.; Ferro, V.; van der Vlag, J.; Berden, J. H. M.; Parish, C. R.; Power, D. A. J. Am. Soc. Nephrol. 2004, 15, 2882.
[15] Ferro, V.; Li, C.; Fewings, K.; Palermo, M. C.; Linhardt, R. J.; Toida, T. Carbohydr. Res. 2002, 337, 139.
[16] Yu, G.; Gunay, N. S.; Linhardt, R. J.; Toida, T.; Fareed, J.; Hoppensteadt, D. A.; Shadid, H.; Ferro, V.; Li, C.; Fewings, K.; Palermo, M. C.; Podger, D. Eur. J. Med. Chem. 2002, 37, 783.
[17] Ferro, V.; Fewings, K.; Palermo, M. C.; Li, C. Carbohydr. Res. 2001, 332, 183.
[18] Parolis, L. A. S.; Parolis, H.; Kenne, L.; Meldal, M.; Bock, K. Carbohydr. Res. 1998, 309, 77.
[19] Gunay, N. S.; Linhardt, R. J. Planta Med. 1999, 65, 301.
[20] Ferro, V.; Hammond, E.; Fairweather, J. K. Mini-Rev. Med. Chem. 2004, 4, 693.
[21] Alban, S.; Franz, G. Biomacromolecules 2001, 2, 354.
[22] Foxall, C.; Wei, Z.; Schaefer, M. E.; Casabonne, M.; Fugedi, P.; Peto, C.; Castellot, J. J., Jr; Brandley, B. K. J. Cell. Physiol. 1996, 168, 657.
[23] Fugedi, P.; Tyrrell, D. J.; Tressler, R. J.; Stack, R. J.; Ishihara, M. 5,739,115, 1998.
[24] Katsuraya, K.; Nakashima, H.; Yamamoto, N.; Uryu, T. Carbohydr. Res. 1999, 315, 234.
[25] Wessel, H. P. Topics Curr. Chem. 1997, 187, 215.
[26] Chen, L.; Kong, F. J. Carbohydr. Chem. 2002, 21, 341.
[27] Mori, M.; Ito, Y.; Ogawa, T. Carbohydr. Res. 1989, 192, 131.
[28] Kerekgyarto, J.; Kamerling, J. P.; Bouwstra, J. B.; Vliegenthart, J. F.; Liptak, A. Carbohydr. Res. 1989, 186, 51.

[29] Jacobsen, S. *Acta Chem. Scand. Ser. B, Org. Chem. Biochem.* 1984, B38, 157.
[30] Ogawa, T.; Sasajima. *Carbohydr. Res.* 1981, 93,53.
[31] Ogawa, T.; Sasajima. *Carbohydr. Res.* 1981, 97, 205.
[32] Garegg, P. J.; Olsson, L.; Oscarson, S. *Bioorg. Med. Chem.* 1996, 4, 1867.
[33] Fairweather, J. K.; Karoli, T.; Ferro, V. Bioorg. *Med. Chem.* 2004, 12, 6063.
[34] Karlsson, R.; Roos, H.; Fägerstam, L.; Persson, B. *Methods* 1994, 6, 99.
[35] Gunalp, A. *Proc. Soc. Exp. Biol. Med.* 1965, 118, 85.
[36] Holland, T. C.; Homa, F. L.; Marlin, S. D.; Levine, M.; Glorioso, J. *J. Virol.* 1984, 52, 566.

The invention claimed is:
1. A compound of the general formula:

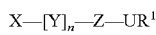

wherein:
X, Y and Z are each the same monosaccharide unit with a group UR bonded via a single or multiple bond to each non-linking carbon of X, Y and Z, except carbon-1 of monosaccharide Z which bears $UR^1$ bonded via a single or multiple bond;
n is an integer having a value of 0-6;
each U is independently C, N, S O CO, COO, NO, $NO_2$, S(O), or S(O)O;
each R is independently $SO_3M$ or H, where M is any pharmaceutically acceptable cation, or is any alkyl, aryl, acyl, aroyl, alkyl sulfonyl, aryl sulfonyl, PEG, an alkoxy PEG, H or the group

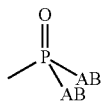

where independently in each AB group, A is O or NH, and B is H, or M where M is any pharmaceutically acceptable cation, an alkyl, an aryl group, or R together with U is $N_3$; and
$R^1$ is $SO_3M$, H, aryl, acyl, aroyl, alkyl sulfonyl, aryl sulfonyl, PEG or an alkoxy PEG, or $R^1$ together with U is $N_3$ or a substituted triazole, or a substituted tetrazole, or a substituted aryl, or a substituted heteroaryl;
with the provisos that:
at least one UR is $N_3$; and
at least 50% of the R groups are $SO_3M$.
2. The compound of claim 1, wherein M is sodium.
3. The compound of claim 1, wherein n is 3.
4. The compound of claim 1, wherein 70 to 100% of the R groups comprise $SO_3M$.
5. A pharmaceutical or veterinary composition for the treatment in a mammalian subject of a disorder resulting from one or more of: angiogenesis, metastasis, inflammation, coagulation, thrombosis, raised blood triglyceride levels, proliferative retinopathy, or solid tumor, HSV-1 infection, or cardiovascular disease, which composition comprises at least one compound according to claim 1 together with a pharmaceutically or veterinarially acceptable carrier or diluent for said at least one compound.
6. The composition according to claim 5 which further includes a pharmaceutically or veterinarially acceptable excipient, buffer, stabiliser, isotonicising agent, preservative or antioxidant.

7. The composition according to claim 5, wherein said compound is present therein as an ester, a free acid or base, or having one or more lipid substituents.
8. A method for the treatment in a mammalian subject of a disorder resulting from one or more of: angiogenesis, metastasis, inflammation, coagulation, thrombosis, raised blood triglyceride levels, proliferative retinopathy, or solid tumor, HSV-1 infection, or cardiovascular disease, which method comprises administering to the subject an effective amount of at least one compound according to claim 1, or a composition comprising said at least one compound.
9. The method according to claim 8 wherein said mammalian subject is a human subject.
10. The method according to claim 8, wherein said disorder resulting from angiogenesis is a proliferative retinopathy or angiogenesis resulting from the growth of a solid tumour.
11. The method according to claim 8, wherein said disorder resulting from inflammation is rheumatoid arthritis, multiple sclerosis, inflammatory bowel disease, allograft rejection or chronic asthma.
12. The method according to claim 8, wherein said disorder resulting from coagulation or thrombosis is deep venous thrombosis, pulmonary embolism, thrombotic stroke, peripheral arterial thrombosis, unstable angina or myocardial infarction.
13. A compound of the general formula:

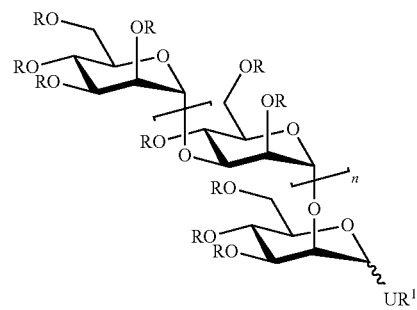

wherein:
n is an integer having a value of 0-6;
U is C, N, S O, CO, COO, NO, $NO_2$, S(O), or S(O)O;
each R is independently $SO_3M$ or H, where M is any pharmaceutically acceptable cation or is any alkyl, aryl, acyl, aroyl, alkyl sulfonyl, aryl sulfonyl, PEG, an alkoxy PEG, H or the group

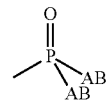

where independently in each AB group, A is O or NH, and B is H, or M where M is any pharmaceutically acceptable cation, an alkyl, aryl group or or R together with U is $N_3$; and
$R^1$ is $SO_3M$, H, alkyl, aryl, acyl, aroyl, alkyl sulfonyl, aryl sulfonyl, PEG or an alkoxy PEG, or $R^1$ together with U is $N_3$ or a substituted triazole, or a substituted tetrazole, or a substituted aryl, or a substituted heteroaryl;
with the provisos that:
at least one R is $N_3$; and
at least 50% of the R groups are $SO_3M$.

14. The compound of claim 13, wherein M is sodium.

15. The compound of claim 13, wherein n is 3.

16. The compound of claim 13, wherein $R^1$ is n-octyl.

17. The compound of claim 13, wherein 70 to 100% of the R groups comprise $SO_3M$.

18. A pharmaceutical or veterinary composition for the treatment in a mammalian subject of a disorder resulting from one or more of: angiogenesis, metastasis, inflammation, coagulation, thrombosis, raised blood triglyceride levels, proliferative retinopathy, or solid tumor, HSV-1 infection, or cardiovascular disease, which composition comprises at least one compound according to claim 13 together with a pharmaceutically or veterinarially acceptable carrier or diluent for said at least one compound.

19. The composition according to claim 18 which further includes a pharmaceutically or veterinarially acceptable excipient, buffer, stabiliser, isotonicising agent, preservative or antioxidant.

20. The composition according to claim 18, wherein said compound is present therein as an ester, a free acid or base, or having one or more lipid substituents.

21. A method for the treatment in a mammalian subject of a disorder resulting from one or more of: angiogenesis, metastasis, inflammation, coagulation, thrombosis, raised blood triglyceride levels, proliferative retinopathy, or solid tumor, HSV-1 infection, or cardiovascular disease, which method comprises administering to the subject an effective amount of at least one compound according to claim 13, or a composition comprising said at least one compound.

22. The method according to claim 21 wherein said mammalian subject is a human subject.

23. The method according to claim 21, wherein said disorder resulting from angiogenesis is a proliferative retinopathy or angiogenesis resulting from the growth of a solid tumour.

24. The method according to claim 21, wherein said disorder resulting from inflammation is rheumatoid arthritis, multiple sclerosis, inflammatory bowel disease, allograft rejection or chronic asthma.

25. The method according to claim 21, wherein said disorder resulting from coagulation or thrombosis is deep venous thrombosis, pulmonary embolism, thrombotic stroke, peripheral arterial thrombosis, unstable angina or myocardial infarction.

26. A pharmaceutical or veterinary composition for the treatment in a mammalian subject of a disorder resulting from one or more of: angiogenesis, metastasis, inflammation, coagulation, thrombosis, raised blood triglyceride levels, proliferative retinopathy, or solid tumor, HSV-1 infection, or cardiovascular disease, which composition comprises at least one compound of the general formula:

$$X-[Y]_n-Z-UR^1$$

wherein:
X, Y and Z are each the same monosaccharide unit with a group UR bonded via a single or multiple bond to each non-linking carbon of X, Y and Z, except carbon-1 of monosaccharide Z which bears $UR^1$ bonded via a single or multiple bond;
n is an integer having a value of 0-6;
each U is independently C, N, S or O, CO, COO, NO, $NO_2$, S(O), S(O)O;
each R is independently $SO_3M$, where M is any pharmaceutically acceptable cation, or is any alkyl, aryl, acyl, aroyl, alkyl sulfonyl, aryl sulfonyl, PEG, an alkoxy PEG, H or the group

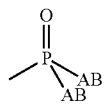

where independently in each AB group, A is O or NH, and B is H, or M where M is any pharmaceutically acceptable cation, an alkyl, an aryl group or R together with U is $N_3$;
$R^1$ is alkyl;
with the proviso that at least 50% of the R groups are $SO_3M$.

27. The composition according to claim 26 which further includes a pharmaceutically or veterinarially acceptable excipient, buffer, stabiliser, isotonicising agent, preservative or antioxidant.

28. The composition according to claim 26, wherein said compound is present therein as an ester, a free acid or base, having one or more lipid substituents.

29. A method for the treatment in a mammalian subject of a disorder resulting from one or more of: angiogenesis, metastasis, inflammation, coagulation, thrombosis, raised blood triglyceride levels, proliferative retinopathy, solid tumor, HSV-1 infection, or cardiovascular disease, which method comprises administering to the subject an effective amount of at least one compound of the general formula:

$$X-[Y]_n-Z-UR^1$$

wherein:
X, Y and Z are each the same monosaccharide unit with a group UR bonded via a single or multiple bond to each non-linking carbon of X, Y and Z, except carbon-1 of monosaccharide Z which bears $UR^1$ bonded via a single or multiple bond;
n is an integer having a value of 0-6;
each U is independently C, N, S or O, CO, COO, NO, $NO_2$, S(O), S(O)O;
each R is independently $SO_3M$, where M is any pharmaceutically acceptable cation, or is any alkyl, aryl, acyl, aroyl, alkyl sulfonyl, aryl sulfonyl, PEG, an alkoxy PEG, H or the group

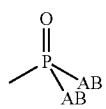

where independently in each AB group, A is O or NH, and B is H, or M where M is any pharmaceutically acceptable cation, an alkyl, an aryl group or R together with U is $N_3$;
$R^1$ is alkyl;
with the proviso that at least 50% of the R groups are $SO_3M$; or a composition comprising said at least one compound.

30. The method according to claim 29 wherein said mammalian subject is a human subject.

31. The method according to claim 29, wherein said disorder resulting from angiogenesis is a proliferative retinopathy or angiogenesis resulting from the growth of a solid tumour.

32. The method according to claim 29, wherein said disorder resulting from inflammation is rheumatoid arthritis, multiple sclerosis, inflammatory bowel disease, allograft rejection or chronic asthma.

33. The method according to claim 29, wherein said disorder resulting from coagulation or thrombosis is deep venous thrombosis, pulmonary embolism, thrombotic stroke, peripheral arterial thrombosis, unstable angina or myocardial infarction.

34. A compound, wherein said compound is PG505: 2,3,4,6-Tetra-O-sulfono-α-D-glucopyranosyl-(1→4)-2,3,6-tri-O-sulfono-α-D-glucopyranosyl-(1→4)-2,3,6-tri-O-sulfono-α-D-glucopyranosyl-(1→4)-2,3,6-tri-O-sulfono-α-D-glucopyranosyl-(1→4)-2,3,6-tri-O-sulfono-α-D-glucopyranosyl-(1→4)-1-azido-2,3,6-tri-O-sulfono-α-D-glucopyranose, hexadecasodium salt.

35. A compound according to claim 2, wherein said compound is PG515: Benzyl (6-Azido-6-deoxy-2,3,4-tri-O-sulfono-α-D-mannopyranoside)-(1,3)-(2,4,6-tri-O-sulfono-α-D-mannopyranoside)-(1,3)-(2,4,6-tri-O-sulfono-α-D-mannopyranoside)-(1,2)-3,4,6-tri-O-sulfono-α-D-mannopyranoside, dodecasodium salt.

* * * * *

UNITED STATES PATENT AND TRADEMARK OFFICE
CERTIFICATE OF CORRECTION

| | | |
|---|---|---|
| PATENT NO. | : 8,173,606 B2 | Page 1 of 1 |
| APPLICATION NO. | : 12/960145 | |
| DATED | : May 8, 2012 | |
| INVENTOR(S) | : Ferro et al. | |

It is certified that error appears in the above-identified patent and that said Letters Patent is hereby corrected as shown below:

In the Claims

In Claim 1, at Col. 45, line 27: replace "S O" by --S, O,--

In Claim 1, at Col. 45, line 29: delete "or H"

In Claim 13, at Col. 46, line 45: after "N, S" insert --,--

In Claim 13, at Col. 46, line 46: delete "or H"

In Claim 13, at Col. 46, line 59: after "alkyl" insert --group--

In Claim 13, at Col. 46, line 59: before "aryl" insert --an--

In Claim 13, at Col. 46, line 59: delete the second instance of "or"

In Claim 13, at Col. 46, line 59: replace "U" by --O--

In Claim 13, at Col. 46, line 66: after "R" insert --together with O--

Signed and Sealed this
Twenty-second Day of July, 2014

Michelle K. Lee
*Deputy Director of the United States Patent and Trademark Office*